United States Patent
Woodbury et al.

(10) Patent No.: US 10,407,663 B2
(45) Date of Patent: *Sep. 10, 2019

(54) OBTAINING MULTIPOTENT AMNION-DERIVED STEM CELL (ADSC) FROM AMNIOTIC MEMBRANE TISSUE WITHOUT ENZYMATIC DIGESTION

(71) Applicant: Rutgers, The State University of New Jersey, New Brunswick, NJ (US)

(72) Inventors: Dale Woodbury, Middletown, NJ (US); Akiva J. Marcus, Teaneck, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/100,593

(22) Filed: Aug. 10, 2018

(65) Prior Publication Data

US 2019/0040355 A1 Feb. 7, 2019

Related U.S. Application Data

(63) Continuation of application No. 14/660,572, filed on Mar. 17, 2015, now Pat. No. 10,066,202, which is a continuation of application No. 12/306,871, filed as application No. PCT/US2007/072356 on Jun. 28, 2007, now Pat. No. 8,980,630.

(60) Provisional application No. 60/816,987, filed on Jun. 28, 2006, provisional application No. 60/930,782, filed on May 18, 2007.

(51) Int. Cl.
*C12N 5/02* (2006.01)
*C12N 5/073* (2010.01)
*C12N 5/0793* (2010.01)
*C12N 5/077* (2010.01)
*C12N 5/071* (2010.01)
*C12N 5/0775* (2010.01)

(52) U.S. Cl.
CPC ........... *C12N 5/0605* (2013.01); *C12N 5/067* (2013.01); *C12N 5/0619* (2013.01); *C12N 5/0653* (2013.01); *C12N 5/0654* (2013.01); *C12N 5/0668* (2013.01); *C12N 2500/84* (2013.01); *C12N 2501/115* (2013.01); *C12N 2501/119* (2013.01); *C12N 2501/12* (2013.01); *C12N 2501/23* (2013.01); *C12N 2506/02* (2013.01); *C12N 2506/1353* (2013.01); *C12N 2509/00* (2013.01)

(58) Field of Classification Search
CPC .. C12N 5/0605; C12N 5/0619; C12N 5/0653; C12N 5/0654; C12N 5/067; C12N 2500/84; C12N 2501/115; C12N 2501/119; C12N 2501/12; C12N 2501/23; C12N 2506/02; C12N 2506/1353; C12N 2509/00; C12N 5/0668
See application file for complete search history.

(56) References Cited

U.S. PATENT DOCUMENTS

| 8,980,630 B2 | 3/2015 | Woodbury et al. |
| 2005/0118712 A1 | 6/2005 | Tsai et al. |
| 2007/0243172 A1 | 10/2007 | Ra et al. |

FOREIGN PATENT DOCUMENTS

| WO | 0073421 A2 | 12/2000 |
| WO | 02064755 A2 | 8/2002 |
| WO | 2005042703 A2 | 5/2005 |
| WO | 2006019357 A1 | 2/2006 |

OTHER PUBLICATIONS

Zhao, et al., Human Amniotic Mesenchymal Cells Have Some Characteristics of Cardiomyocytes Transplantation, Mar. 2005, vol. 79, pp. 208-214.
Tsai, et al., Isolation of Human Multipotent Mesenchymal Stem Cells from Second-Trimester Amniotic Fluid using a Novel Two-Stage Culture Protocol Human reproduction, 2004, vol. 19, pp. 1450-1456.
Sakuragawa et al., Human Amnion Mesenchyme Cells Express Phenotypes of Neuroglial Progenitor Cells. J Neuroscience Res., 2004, vol. 78, pp. 208-214.
Grueterich et al., Connexin 43 Expression and Proliferation of Human Limbal Epithelium on Intact and Denuded Amniotic Membrane. Investigative Ophthalmology and Vicsula Science, 2002, vol. 43,pp. 63-71.
Ji et al., Cryopreservation of Adherent Human Embryonic Stem Cells Lin. Biotechnology and Bioengineering, 2004, vol. 88, pp. 299-312.
Zhao et al., Human Amniotic Mesenchymal Cells Have Some Characteristics of Cardiomyocytes.Transplantation, Mar. 2005, vol. 79, pp. 528-535.
Casey et al., Interstitial Collagen Synthesis and Processing in Human Amnion: A Property of the Mesenchymal Cells. Biology of Reproduction, 1996, vol. 55, pp. 1253-1260.
Soncini et al., Isolation and characterization of mesenchymal cells from human fetal membranes. J. Tissue Engeering Regenerative Medicine, 2007, vol. 1 pp. 296-305.
Kim et al., Ex Vivo Characteristics of Human Amniotic Membrane-Derived Stem Cells. Cloning and Stem Cells, 2007, vol. 9, pp. 581-594.

(Continued)

*Primary Examiner* — Titilayo Moloye
(74) *Attorney, Agent, or Firm* — Miller, Matthias & Hull LLP

(57) ABSTRACT

The present invention relates to stem cells obtained from the amnion and their methods of obtaining and culturing. The present invention further relates to compositions comprising amnion-derived stem cells (ADSCs) and to methods of using ADSCs.

3 Claims, 14 Drawing Sheets

Specification includes a Sequence Listing.

(56) References Cited

OTHER PUBLICATIONS

Kim et al., Amniotic mesenchymal stem cells have robust angiogenic properties and are effective in treating hindlimb ischaemia. Cardiovascular Research, 2012, vol. 93, pp. 525-534.
Hu et al., Progress in studies on the characteristics of human amnion mesenchymal cells. Progress in Natural Science, 2009, vol. 19, pp. 1047-1052.
Roubelakis et al., Amniotic Fluid and AmnioticMembrane Stem Cells: Marker Discovery. Stem Cells International, vol. 2012, pp. 1-9, doi: 10.1155/2012/10783.
De Rosa et al., Amniotic Fluid-Derived Mesenchymal Stem Cells Lead to Bone Differentiation when Cocultured with Dental Pulp Stem Cells, Tissue Engineering; Part Am vol. 17, pp. 645-654, 2011.
Deng et al., n Vitro Differentiation of Human Marrow Stromal Cells into Early Progenitors of Neural Cells by Conditions That Increase Intracellular Cyclic AMP. Biochm. Biophys. Res. Comm., vol. 282, pp. 148-152, 2001.
Tamagawa et al., "Establishment and Characterization of a Pluripotent Stem Cell Line Derived from Human Amniotic membranes and Initiation of Germ Layers in vitro," Human Cell (2004): vol. 17, No. 3; pp. 125-130.
Miki et al., "Stem Cell Characteristics of Amniotic Epithelial Cells," Stem Cells (2005): vol. 23; pp. 1549-1559.
Marcus et al., "Isolation, characterization, and differentiation of stem cells derived from the rat amniotic membrane," Differentiation (2008): vol. 76; pp. 130-144.
Marcus et al., "Fetal stem cells from extra-embryonic tissues: do not discard," J. Cell. Mol. Med. (2008): vol. 12, No. 3; pp. 730-742.

Figure 3.

OBTAINING MULTIPOTENT AMNION-DERIVED STEM CELL (ADSC) FROM AMNIOTIC MEMBRANE TISSUE WITHOUT ENZYMATIC DIGESTION

FIELD OF THE INVENTION

The present invention relates to stem cells obtained from the amnion and their methods of obtaining and culturing. The present invention further relates to compositions comprising amnion-derived stems cells (ADSCs) and to methods of using ADSCs.

BACKGROUND OF THE INVENTION

Stem cells have been considered as potential treatments for debilitating diseases of various etiologies, including diabetes, Parkinson's disease and cardiovascular disease. Thus, a critical goal is to define the spectrum of stem cell types displaying characteristics advantageous for the treatment of selected disorders. While the pluripotency and self-renewal of embryonic stem cells is well-recognized, the potential of adult and fetal stem cells has been appreciated only recently.

Stem cells have the potential to develop into many different cell types in the body. Stem cells can theoretically divide without limit to replenish other cells. When a stem cell divides, each new cell has the potential to either remain a stem cell or become another type of cell with a more specialized function, such as a muscle cell, a red blood cell, or a brain cell. Stem cells are often classified as totipotent, pluripotent, and multipotent. Totipotent stem cells (e.g., a zygote) give rise to both the fetus and the extraembryonic tissues. Pluripotent stem cells can give rise to any type of cell except for the extraembryonic tissues (e.g., placenta). Multipotent stem cells can give rise to two or more different cell types but only within a given organ or tissue type. In contrast to stem cells, progenitor cells are unable to self-renew and they give rise to only a few cell types.

A central dogma in embryonic development is that cells undergo a process of fate restriction and commitment. This process begins with the development of the blastocyst; a structure composed of an outer trophoblast layer and an undifferentiated inner cell mass (ICM).

The ICM is the source of embryonic stem cells (ES cells), which are regarded as the quintessential stem cell population (Evans and Kaufman, 1981; Martin, 1981). ES cells demonstrate long-term self-renewal and differentiate into multiple cell types in vitro and in vivo (Smith, 2001; Thomson et al., 1998; Bradley et al., 1984; Amit et al., 2000).

Due to their remarkable in vitro and in vivo plasticity, ES cells have been regarded as the "gold standard" for cell replacement therapy and regenerative medicine. Although the therapeutic potential of ES cells is promising, a number of issues must be addressed prior to clinical use. Ethical concerns and in some cases governmental policies restrict the isolation and cultivation of human ES cells. From a safety perspective, ES cells often form tumors following transplantation into rodents (Evans and Kaufman, 1983). Furthermore, ES cells might not be able to overcome the immunological incompatibility that exists between host and grafted cells (Keller, 2005). With all these unresolved issues many investigators have turned to adult and fetal tissue in search of less controversial stem and precursor populations.

The wide distribution and plasticity of adult stem cells has only recently been appreciated. In addition to the well known stem cells of the adult marrow lymphohematopoietic (Shizuru et al., 2005; Krause et al., 2001) and stromal mesenchymal lineages (Prockop, 1997; Jiang et al., 2002), adult stem cells have been identified in fat (Zuk et al., 2001), liver (Theise et al., 1999), muscle (Lee et al., 2000), and the central nervous system (Reynolds and Weiss, 1992; Morshead et al., 1994; Doetsch et al., 1999) and skin (Toma et al., 2001). Recent reports suggest that the differentiation of adult stem cells is not restricted to derivatives of the tissue in which they reside. Landmark studies have demonstrated that adult stem cells can differentiate into progeny of other embryonic germ layers, a process termed transgerminal differentiation. For example, ectodermal neural stem cells can differentiate into mesenchymal derivatives, including blood (Bjornson et al., 1999), muscle (Galli et al., 2000) and endothelial cells (Wurmser et al., 2004). The plasticity exhibited by adult stem cells has provided hope for the development of new autologous cellular therapies.

Adult stem cells may offer advantages over ES cells; however, their potential use in cell replacement therapies is not without obstacles. Many reports have questioned the plasticity of adult stem cells. Several studies have suggested that in vitro and in vivo transgerminal plasticity is the result of cell fusion rather than actual differentiation (Terada et al., 2002; Ying et al., 2002; Wang et al., 2003). In contrast, others have confirmed in vivo transdifferentiation of marrow cells in the absence of cell fusion (Tran et al., 2003; Pochampally et al., 2004; Sato et al., 2005). It has also recently been demonstrated that MSCs transplanted into the adult brain fail to survive. Even more disconcerting, these cells transferred their cellular labels (bromodeoxyuridine and bis benzamide) to endogenous glia and neural cells, giving a false representation of donor cell plasticity (Coyne et al., 2006; Burns et al., 2006). These apparent contradictory results have raised important issues concerning the nature of adult stem cell plasticity and the broader therapeutic potential they represent.

Fetal stem cells may offer a number of therapeutic advantages over ES and adult stem cells, making them well suited for cell replacement therapy. Fetal stem cells are easily accessible from extra-embryonic tissue that is normally discarded at birth, including the umbilical cord (Nakahata and Ogawa, 1982; Knudtzon, 1974) and placenta (Kaviani et al., 2002; Yen et al., 2005), circumventing many of the ethical concerns presented by ES cell research. Fetal stem cells grow rapidly in culture and exhibit plasticity similar to ES cells, but without documented tumor formation in vivo (Miki et al., 2005). Moreover, fetal stem cells might be more amenable to transplantation due to their immunoprivileged characteristics (Li et al., 2005; Kubo et al., 2001).

The present invention describes the identification and characterization of a fetal stem cell population isolated from explants of amniotic membrane. These amnion-derived stem cells (ADSCs) fulfill all criteria of a stem cell population, including clonality, which has proven difficult in previous studies of putative fetal stem cells (Woodbury et al., 2006; Miki et al., 2005).

SUMMARY OF THE INVENTION

The present invention provides stem cells from the amnion. One aspect of the invention provides a method for obtaining an amnion-derived stem cell (ADSC) comprising: a. separating an amniotic membrane tissue sample from chorion of a mammalian embryo; b. culturing the amniotic membrane tissue sample; c. preparing a single-cell culture of ADSC isolated from the amniotic membrane tissue sample; d. culturing the ADSC; and e. obtaining or isolating the ADSCs. In one embodiment the amniotic membrane tissue sample is washed and fragmented after step a. and before step b. In one embodiment amniotic membrane tissue sample is cultured in Dulbecco's modified Eagle's medium (DMEM) supplemented with 20% fetal bovine serum (FBS).

In one embodiment the mammal is mouse, rat, or human.

In one embodiment the single-cell culture is prepared by enzymatically digesting the amniotic membrane tissue sample.

In one embodiment the ADSC is multipotent. In one embodiment the ADSC is pluripotent.

In one aspect the invention provides a multipotent ADSC obtained by the method of the present invention.

In one aspect the invention provides a pluripotent ADSC obtained by the method of the present invention.

In one aspect the invention provides an isolated ADSC having at least one of the following characteristics: a. positive for cell markers CD29 and CD90; and b. negative for cell markers CD45 and CD11b. In one embodiment the ADSC has the following characteristics: a. positive for cell markers CD29 and CD90; and b. negative for cell markers CD45 and CD11b.

In one aspect the invention provides an isolated ADSC which expresses at least one of the genes selected from the group consisting of Telomerase, Nanog, Sox2, □-III-Tubulin, NF-M, MAP2, APP, GLUT, NCAM, NeuroD, Nurrl, GFAP, NG2, Olig1, Alkaline Phosphatase, Vimentin, Osteonectin, Osteoprotegrin, Osterix, Adipsin, Erythropoietin, SM22-α, HGF, c-MET, α-1-Antriptrypsin, Ceruloplasmin, AFP, PEPCK 1, BDNF, NT-4/5, TrkA, BMP2, BMP4, FGF2, FGF4, PDGF, PGF, TGFα, TGFβ, and VEGF.

In one embodiment the ADSC expresses Telomerase, Nanog, Sox2, β-III-Tubulin, NF-M, MAP2, APP, GLUT, NCAM, NeuroD, Nurrl, GFAP, NG2, Olig1, Alkaline Phosphatase, Vimentin, Osteonectin, Osteoprotegrin, Osterix, Adipsin, Erythropoietin, SM22-α, HGF, c-MET, α-1-Antriptrypsin, Ceruloplasmin, AFP, PEPCK 1, BDNF, NT-4/5, TrkA, BMP2, BMP4, FGF2, FGF4, PDGF, PGF, TGFα, TGFβ, and VEGF.

In one aspect the invention provides a composition comprising an ADSC of the present invention.

In one aspect the invention provides a cryopreserved ADSC of the present invention.

In one aspect the invention provides a method of treating a patient comprising administering to the patient a therapeutically effective amount of a ADSC of the present invention.

In one aspect the invention provides a method for obtaining an ADSC comprising isolating an ADSC which expresses at least one of the genes selected from the group consisting of Telomerase, Nanog, Sox2, β-III-Tubulin, NF-M, MAP2, APP, GLUT, NCAM, NeuroD, Nurrl, GFAP, NG2, Olig1, Alkaline Phosphatase, Vimentin, Osteonectin, Osteoprotegrin, Osterix, Adipsin, Erythropoietin, SM22-α, HGF, c-MET, α-1-Antriptrypsin, Ceruloplasmin, AFP, PEPCK1, BDNF, NT-4/5, TrkA, BMP2, BMP4, FGF2, FGF4, PDGF, PGF, TGFα, TGFβ, and VEGF. In one embodiment the ADSC expresses Telomerase, Nanog, Sox2, β-III-Tubulin, NF-M, MAP2, APP, GLUT, NCAM, NeuroD, Nurrl, GFAP, NG2, Olig1, Alkaline Phosphatase, Vimentin, Osteonectin, Osteoprotegrin, Osterix, Adipsin, Erythropoietin, SM22-α, HGF, c-MET, α-1-Antliptrypsin, Ceruloplasmin, AFP, PEPCK 1, BDNF, NT-4/5, TrkA, BMP2, BMP4, FGF2, FGF4, PDGF, POP, TGFα, TGFβ, and VEGF.

In one aspect the invention provides a method for neurogenic differentiation of ADSCs, comprising culturing the ADSCs in a medium comprising an effective amount of DMEM pH 7.0 (low glucose) buffered with 2.75 g/liter sodium bicarbonate and 5.96 g/liter HEPES (no serum), 2 mM Valproic Acid, 15 mM Betaine, 2.5 mM Taurine, 175 µM butylated hydroxyanisole, 27 nM selenium, 20 nM progesterone, 10 µM forskolin, 10 nM K252a, 5 Units/ml Heparin, 5 µg/ml Insulin, 1 mM sodium pyruvate, 50 mM α-thioglycerol, and 20 nM Bathocuproinedisulfonic acid, the 10 medium supplemented with 10 ng/ml FGF2 every 48 hours, for about 2 to about 4 weeks to obtain a population of cells having at least one characteristic of a neural cell.

In one aspect the invention provides a method of treating a neurodegenerative disease or a brain or spinal cord injury in a patient, wherein the method comprises administering a therapeutically effective amount of an ADSC of the present invention 15 or a population of neurogenically differentiated cell of the present invention to a patient having a neurodegenerative disease or a brain or spinal cord injury. In one embodiment the neurodegenerative disease is selected from the group consisting of Parkinson's disease, Alzheimer's disease, Pick's disease, Huntington's disease, spingolipidoses, mucosaccharidoses, and amyotrophic lateral sclerosis.

In one aspect the invention provides a method for osteogenic differentiation of ADSCs, comprising a. culturing the ADSCs in a medium comprising an effective amount of DMEM pH 7.4 (High glucose) supplemented with 100 nM Dexamethasone, 10 mM β-glycerol phosphate, 50 µM L-ascorbic acid-2-phosphate for about 2 to about 4 weeks; and b. obtaining a population of cells having at least one characteristic of a bone cell.

In one aspect the invention provides a method of treating a bone disease in a patient, wherein the method comprises administering a therapeutically effective amount of an ADSC of the present invention or the population of osteogenically differentiated cells of the present invention to a patient having the bone disease. In one embodiment the bone disease is selected from the group consisting of osteoporosis, Paget's disease, osteogenesis imperfecta, and osteoarthritis.

In one aspect the invention provides a method for adipose differentiation of ADSCs, comprising a. culturing the ADSCs in a medium comprising an effective amount of 10% FBS/DMEM, 500 µM IBMX, 1 µM dexamethazone stock, 5 µg/mL insulin and 50 µM indomethacin for about 3 days; b. culturing the ADSCs in a medium comprising an effective amount of 10% FBS/DMEM and 5 mg/mL insulin for about 3 days; c. repeating steps a. and b. in order 0 to about 5 times; and d. obtaining a population of cells having at least one characteristic of an adipocyte.

In one aspect the invention provides a method for hepatic differentiation of ADSCs, comprising culturing the ADSCs in a medium comprising an effective amount of 1% FBS/DMEM-LG, 20 ng/ml HOF, 10 ng/ml oncostatin M and 10 ng/ml FGF-4 for about 2 to about 4 weeks to obtain a population of cells having at least one characteristic of a hepatic cell.

In one aspect the invention provides a method of treating a hepatic disease in a patient, wherein the method comprises administering a therapeutically effective amount of an ADSC of the present invention or the population of hepatically differentiated cells of the present invention to a patient having the hepatic disease. In one embodiment the hepatic disease is selected from the group consisting of amebic liver abscess, autoimmune hepatitis, biliary atresia, cirrhosis, coccidioidomycosis; disseminated, delta agent (Hepatitis D), drug-induced cholestasis, hemochromatosis, hepatitis A, hepatitis B, hepatitis C, hepatocellular carcinoma, liver cancer, liver disease due to alcohol, primary biliary cirrhosis, pyogenic liver abscess, Reye's syndrome, sclerosing cholangitis, and Wilson's disease.

In one aspect the invention provides a method of treating a cardiovascular disease in a patient, wherein the method comprises administering a therapeutically effective amount of an ADSC of the present invention to a patient having the cardiovascular disease. In one embodiment the cardiovascular disease is selected from the group consisting of congenital heart defects, peripheral artery disease, arterio-arterial fistula, arteriovenous fistula, cerebral arteriovenous malformations, aortic coarctation, cortriatum, coronary vessel anomalies, patent ductus arteriosus, Ebstein's anomaly, hypoplastic left heart syndrome, levocardia, transposition of great vessels, double outlet right ventricle, tricuspid atresia, persistent truncus arteriosus, and heart septal defects, such as aortopulmonary septal defect, endocardial cushion defects, Lutembacher's Syndrome, ventricular heart septal defects, cardiac tamponade, endocarditis (including bacterial), heart aneurysm, cardiac arrest, congestive heart failure, congestive cardiomyopathy, paroxysmal dyspnea, cardiac edema, post-infarction heart rupture, ventricular septal rupture, heart valve diseases, myocardial diseases, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, cardiovascular syphilis, cardiovascular tuberculosis, affhythmias such as sinus arrhythmia, atrial fibrillation, atrial flutter, bradycardia, extrasystole, Adams-Stokes Syndrome, bundle-branch block, sinoatrial block, long QT syndrome, parasystole, sick sinus syndrome, ventricular fibrillations, tachycardias such as paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia and heart valve diseases such as aortic valve insufficiency, aortic valve stenosis, heart murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

In one aspect the invention provides a method of treating a metabolic disease in a patient, wherein the method comprises administering a therapeutically effective amount of an ADSC of the present invention to a patient having the metabolic disease. In one embodiment the metabolic disease is selected from the group consisting of Phenylketonuria, Alkaptonuria, Ochronosis, Tyrosinemia, Albinism, Histidinemia, Maple syrup urine disease, Propionic acidemia, Methylmalonic acidemia, Isovaleric acidemia, 3-Methylcrotonyl-CoA carboxylase deficiency, Cystinuria, Cystinosis, Hartnup disease, Homocystinuria, Cystathioninuria, N-cetylglutamate synthase deficiency, Carbamoyl phosphate synthetase I deficiency, Ornithine transcarbamylase deficiency, Citrullinemia, Argininosuccinic aciduria, Hyperammonemia, Glutaric acidemia type 1, Sarcosinemia, Lactose intolerance, type I Glycogen storage disease, type II Glycogen storage disease, type III Glycogen storage disease, type IV Glycogen storage disease, type V Glycogen storage disease, type VI Glycogen storage disease, type VII Glycogen storage disease, Fructose intolerance, Essential fructosuria, Galactosemia, PCD, PDHA, Pentosuria, Renal glycosuria, GM2 gangliosidoses, Sandhoff disease, Tay-Sachs disease, GM1 gangliosidoses, Mucolipidosis type IV, Gaucher's disease, Niemann-Pick disease, Farber disease, Fabry's disease, Metachromatic leukodystrophy, Krabbe disease, Neuronal ceroid lipofuscinosis, Batten disease, Cerebrotendineous xanthomatosis Cholesteryl ester storage disease, Wolman disease, Hyperlipidemia, Hypercholesterolemia, Familial hypercholesterolemia, Xanthoma, Combined hyperlipidemia, Lecithin cholesterol acyltransferase deficiency, Tangier disease, Abetalipoproteinemia, Adrenoleukodystrophy, primary carnitine deficiency, carnitine palmitoyltransferase I deficiency, carnitine palmitoyltransferase II deficiency, carnitine-acylcarnitine translocase deficiency, Wilson's disease, Menkes disease, Haemochromatosis, Acrodermatitis enteropathica, Hypophosphatemia, Hypophosphatasia, Hypermagnesemia, Hypomagnesemia, Hypercalcaemia, Hypocalcaemia, Disorders of calcium metabolism, Hyperuricemia, Lesch-Nyhan syndrome, Xanthinuria, Gilbert's syndrome, Crigler-Najjar syndrome, Dubin-Johnson syndrome, Rotor syndrome, Mucopolysaccharidosis, Hurler Syndrome, Hunter Syndrome, Sanfilippo Syndrome, Morquio Syndrome, Maroteaux-Lamy Syndrome, Sly Syndrome, Mucolipidosis, I-cell disease, Pseudo-Hurler polydystrophy, Aspartylglucosaminuria, Fucosidosis, Alpha-mannosidosis, Sialidosis, Alpha 1-antitrypsin deficiency, Cystic fibrosis, Amyloidosis, Familial Mediterranean fever, and Acatalasia.

In one aspect the invention provides a method of cryopreserving ADSCs comprising: a. washing a population of ADSCs; b. suspending the population of ADSCs in a cryopreservation medium comprising 60% Dulbecco's Modified Eagles Media (DMEM)/30% Fetal Bovine Serum (PBS)/ 10% Dimethyl sulfoxide (DMSO); and c. storing the population at a temperature below about −80° C.

In one aspect the invention provides a method of cryopreserving an amniotic membrane tissue sample comprising: a. washing the amniotic membrane tissue sample; b. suspending the amniotic membrane tissue sample in a cryopreservation medium comprising 60% Dulbecco's Modified Eagles Media (DMEM)/30% Fetal Bovine Serum (PBS)/ 10% Dimethyl sulfoxide (DMSO); and c. storing the population at a temperature below about −80° C.

In one aspect the invention provides a method of cryopreserving ADSCs comprising: a. washing a population of ADSCs; b. suspending the population of ADSCs in a cryopreservation medium comprising 60% DMEM/30% Liforcel serum substitute/10% DMSO; and c. storing the population at a temperature below about −80° C.

In one aspect the invention provides a method of cryopreserving an amniotic membrane tissue sample comprising: a. washing the amniotic membrane tissue sample; b. suspending the amniotic membrane tissue sample in a cryopreservation medium comprising 60% DMEM/30% Liforcel serum substitute/10% DMSO; and c. storing the population at a temperature below about −80° C.

BRIEF DESCRIPTION OF THE DRAWINGS

FIG. 3. Gene Expression Profile of ADSCs: RT-PCR reveals that ADSCs express an array of genes, including: (A) proteins normally associated with stem cells, (B) neuroectodermal structural proteins and transcription factors, (C) mesodermal genes normally expressed in bone, fat and muscle cells, (D) endodermal genes representing the lung and liver, (E) neurotrophins and the nerve growth factor receptor TrkA and (F) various growth factors.

(A) ADSCs maintained in OIM for 6 weeks reveal extensive areas of mineralized matrix deposition (Alizarin red staining).

(B) ADSCs exposed to osteogenic conditions attain cuboidal morphologies and form Alizarin red+ nodules (>).

(C) Alizarin red staining of control cultures demonstrates no areas of mineralized matrix or nodular formation.

(D) RNA extracted at 3 and 6 weeks post-induction reveals an up-regulation of the bone-specific gene osteopontin, and maintained expression of mesenchymal osteonectin. Expression of ectodermal NF-M, endodermal α-1-antitrypsin and the stem cell marker nanog decrease concomitantly. GAPDH is used as a loading control. Adipogenic Differentiation:

(E) Following 3 weeks of culture in AIM, ADSCs accumulate fat droplets (red) as indicated by Oil Red O staining.

(F) High power magnification (>) reveals Oil Red-0+ lipid droplets filling most of the cytoplasm.

(G) Control cultures stained with Oil Red O display no lipid accumulation. Endodermal Differentiation of ADSCs:

(H) ADSCs exposed to HIM for 3 weeks demonstrate the ability to take up Dil-Ac-LDL from culture media (red).

(I) Phase contrast image depicts cobblestone appearance of HIM-treated ADSCs.

(J) Control cultures do not show any Dil-Ac-LDL uptake.

(K) PCR analysis of HIM-treated ADSCs at 2 and 3 weeks post-induction demonstrate the up-regulation of liver specific genes albumin and □-1-antitrypsin. The expression of HNF-3α and GS is maintained throughout the experiment. GAPDH is used as a loading control. Scale bars: a, c, e and g=100 µm; b, h, I and j=50 µm; f=10 µm.

Figure 7:
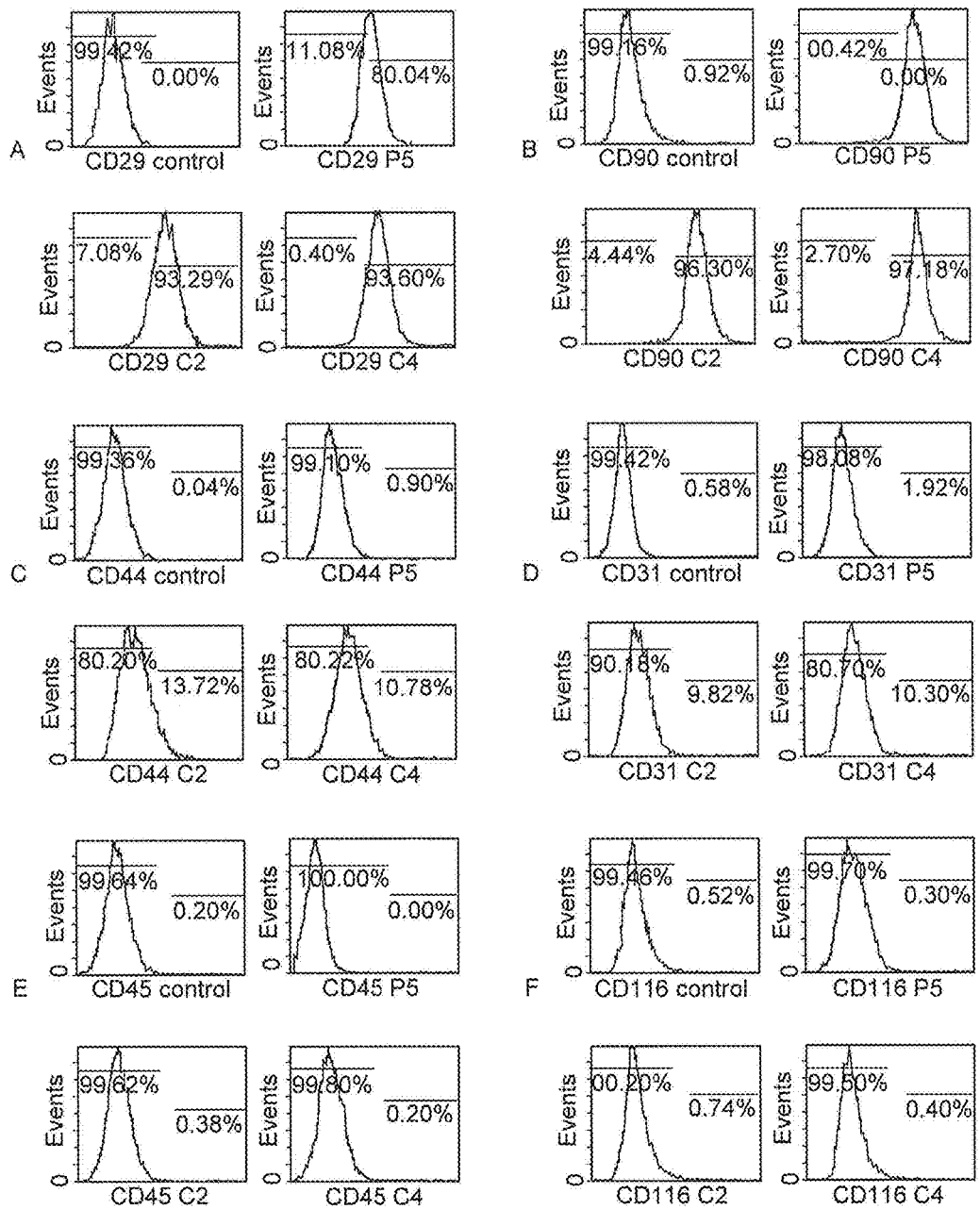

FIG. 7. Flow Cytometric Analysis of Parental and Clonal ADSC Cultures: (A, B) The overwhelming majority (greater than 90%) of parental (PS) and clonal (C2, C4) ADSCs express the mesenchymal cell surface markers CD29 and CD90. (C, D) Variable levels of the CD44 and CD31 are detected within the ADSCs cultures. (E, F) Parental and clonal ADSC populations do not express the lympho-hematopoietic markers CD45 and CD 11b. PS=parental ADSC cultures, C2=ADSC clonal line #2, C4=ADSC clonal cell line #4.

Figure 8:
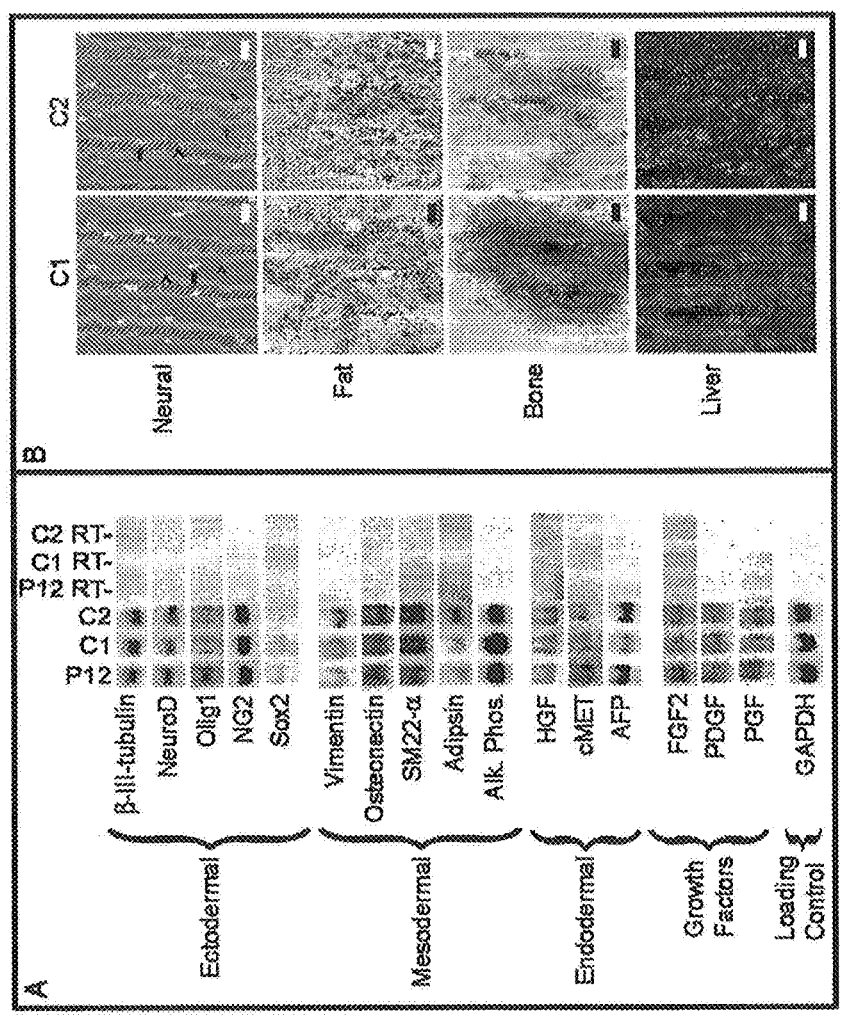

FIG. 8. RT-PCR Analysis and In Vitro Multidifferentiation of ADSC Clonal Lines: (A) The genetic expression profile of two distinct clonal populations (C1, C2) is identical to the parent population. RT-PCR analysis reveals that both clones expressed stem cells markers, growth factors and genes representing all three embryonic layers. (B) Row 1: ADSC clonal cell lines maintain the ability to differentiate into neural cells. Two clonal ADSC cultures exposed to NIM for 1 week attain typical neural morphologies: small, round refractile cell bodies (arrows) elaborating long processes (>) that form networks. Row 2: Clonal ADSC lines accumulate fat droplets, as indicated by positive Oil Red O staining, after culture for 3 weeks in AIM. Row 3: Clonal ADSC populations lay down mineralized matlix, as observed by Alizarin red staining, following 6 weeks of OIM culture. Row 4: Clonal ADSC lines differentiate into presumptive hepatocytes and took up Dil-Ac-LDL after exposure to HIM for 3 weeks. Scale bars: Rows 1_3=100 µm; Row 4=50 µm.

Figure 9:
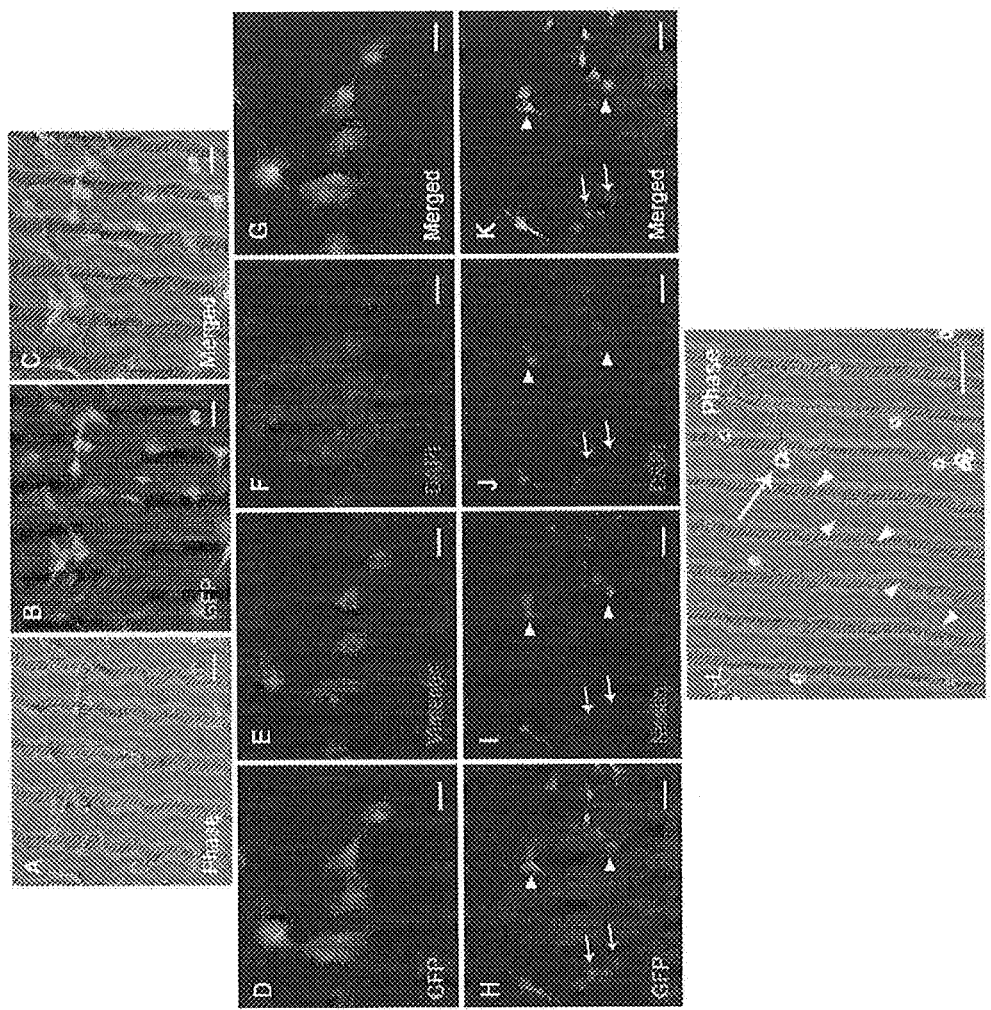

FIG. 9. Characterization of GFP-expressing ADSCs prior to transplantation. (AC) Examination of the same field with phase contrast and fluorescent microscopy reveals uniform expression of GFP in ADSCs. Regardless of the passage number close to 100% of the cells express GFP. (DG) GFP-expressing ADSCs express the mesodermal marker vimentin, while a subset of cells (HK, arrowheads) express the neural progenitor marker nestin. (HK) The majority of ADSCs (arrows) are negative for nestin. (L) After culture in a defined neural induction media GFP+ ADSCs attain a neural morphology, exhibiting round, compact, refractile cell bodies (arrow), while elaborating long processes extending more than 600 µm in length (>'s). Scale Bars: AC=50 µm; DO=100 µm; HL=100 µm.

Figure 10:
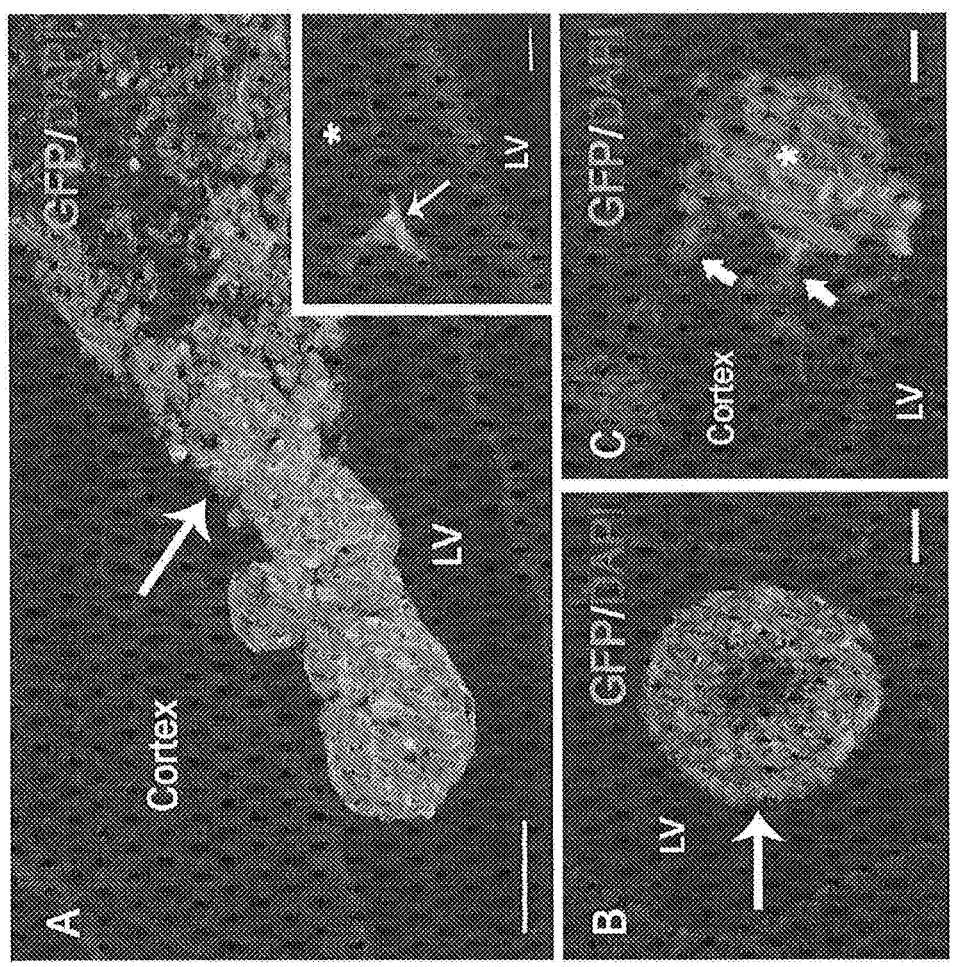

FIG. 10. Infused ADSCs disperse throughout the embryonic ventricular system and form discrete spheres. (A) Sagittal section reveal extensive diffusion of donor ADSCs (arrow) throughout the ventricular system at E16.5 (24 hours post-transplantation). (A, inset, arrow) Some donor cells are observed within the parenchyma of the brain even at this early time point. (B) By El 7.5 donor cells form discrete GFP+ spheres or clusters (arrow) within the lateral ventricles. (C) Some spheres appear to have fused with the walls of the ventlicular cavity. Individual cells (arrows) can be observed migrating into the parenchyma. LV=lateral ventricle, *=cortex. Scale bars: A, B=100 µm; Ainset=20 µm; C=50 µm.

Figure 11:
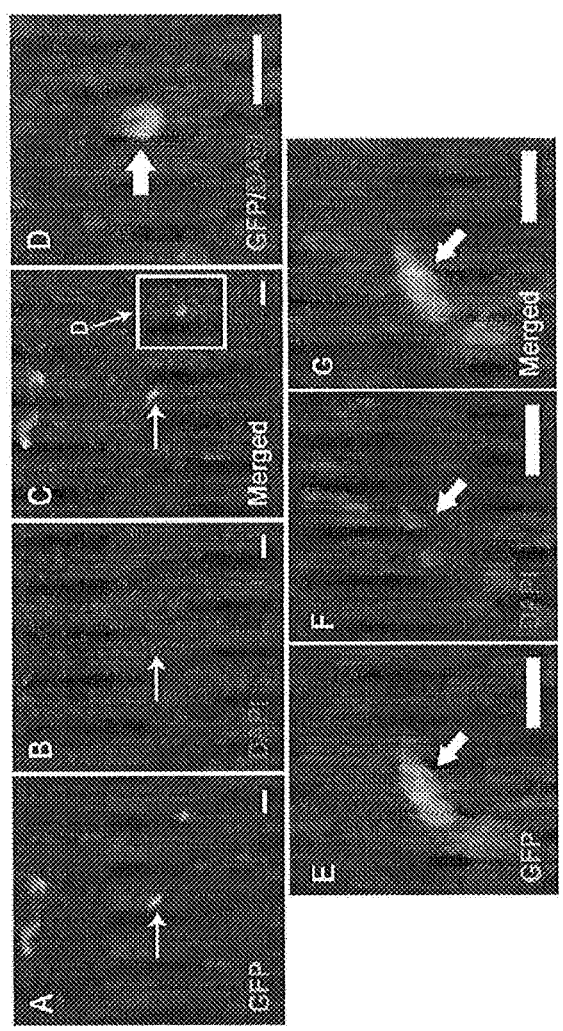

FIG. 11: Distribution of ADSCs at E20.5. (AC) At E20.5 GFP+ ADSCs (arrow) are observed in a number of brain areas, including the cortex. (D) Higher magnification of the box in (C) reveals that a subset of donor cells (arrow) in the brain associate with vascular structures. These cells have crescent morphologies, similar to endogenous endothelial cells. (EG) Donor ADSCs (arrow) are also evident in other brain areas, including the midbrain. Scale bars: AG=20 µm.

Figure 12:
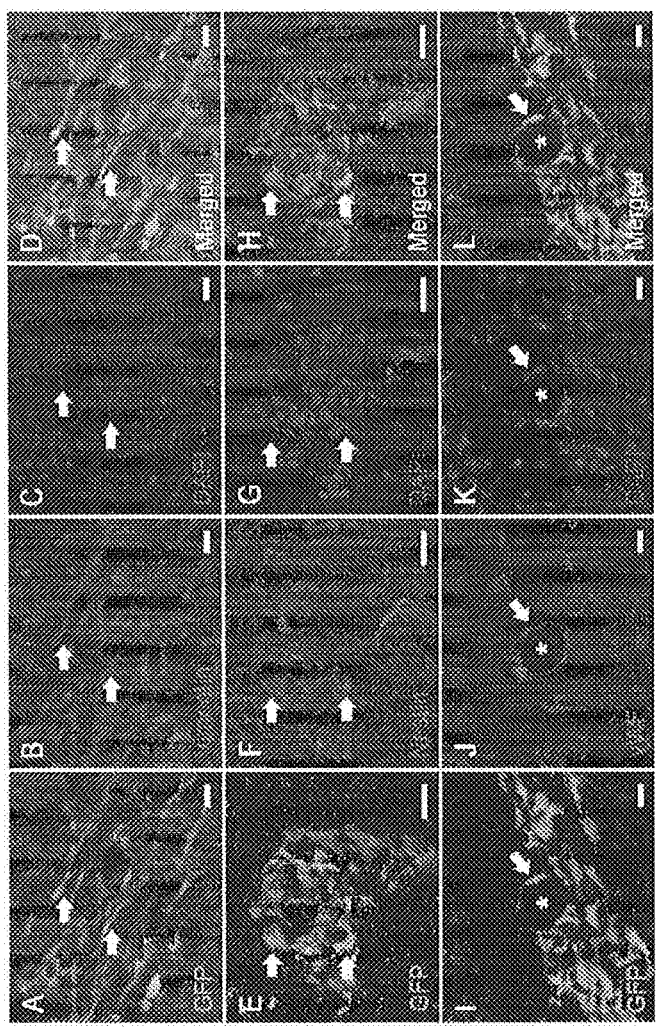

FIG. 12. Morphology and Phenotypic characterization of transplanted ADSCs at one week postnatal. (AD) The majority of transplanted GFP+ ADSCs (arrows) within the cortex attain elongated morphologies and expressed vimentin. (EH) Some donor cells (arrows) are nestin positive and assumed ameboid morphologies. (IJ) A subpopulation of donor cells (arrow) around blood vessels attain crescent morphologies and expressed von Willebrand factor (vWF). *=blood vessel. Scale bar: AL=20 µm.

Figure 13:
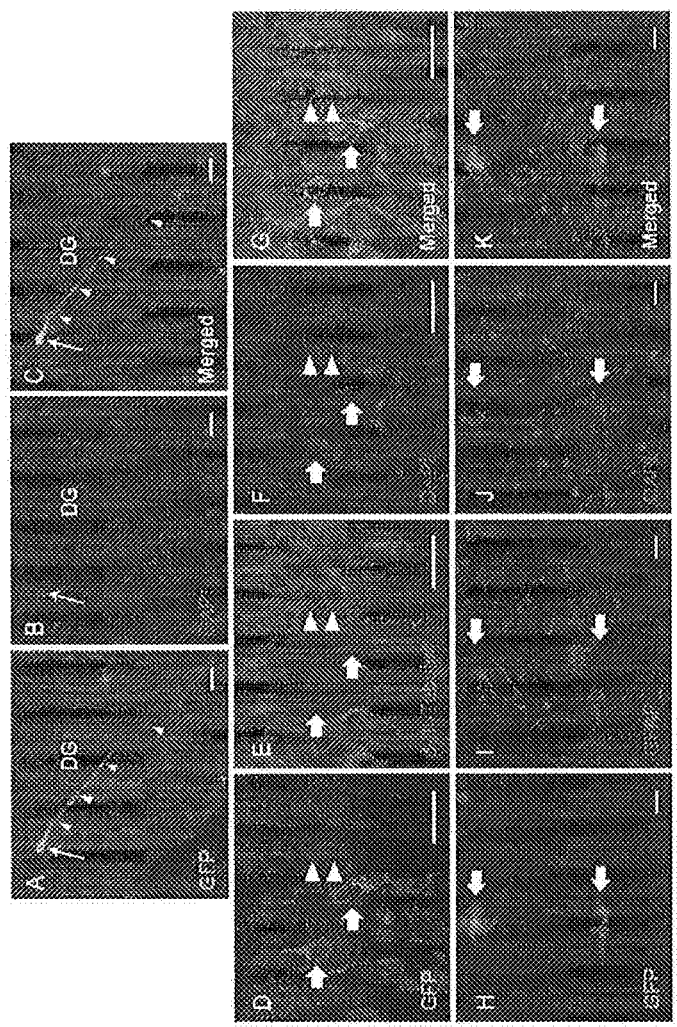

FIG. 13. A subpopulation of transplanted ADSCs assume neuronal morphologies. (AC) At P7 a subset of GFP+ cells in the hippocampal formation assume typical neural morphologies: small cell bodies (arrow) and the elaboration of long processes (arrowheads). (DG) Donor cells (arrows) within the cortex do not express the neuronal protein, 13-III tubule, in contrast to neighboring endogenous cells (arrowheads). (HK) GFP+ ADSCs do not express the atrocity structural protein GFAP. DG=Dentate Gyros. Scale bar: AK=20 µm.

Figure 14:
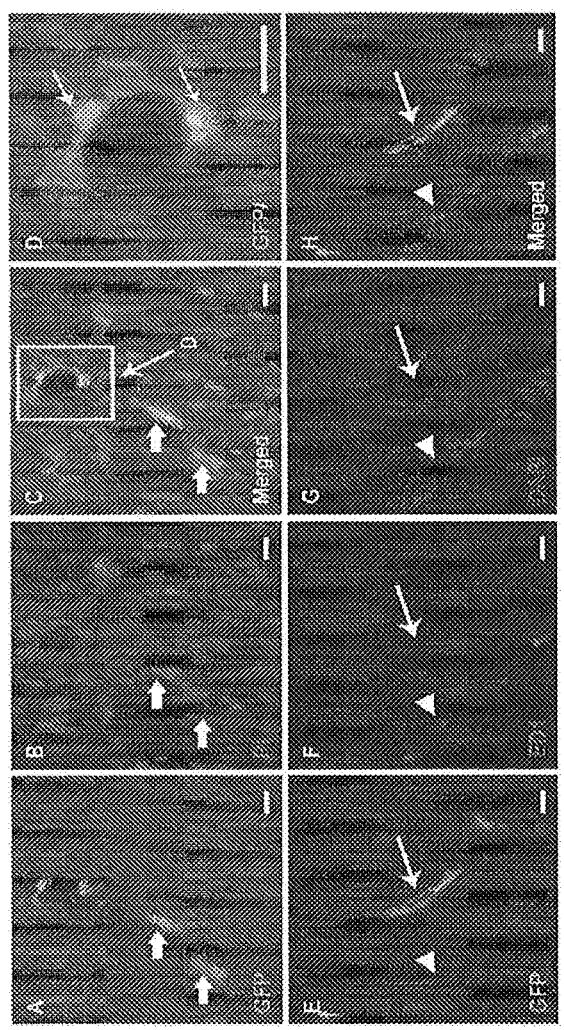

FIG. 14. Long-term survival of transplanted ADSCs in the neocortex. (AC) In utero transplanted ADSCs (arrows) survive 2.5 months in the neocortex of recipient animals. (D) Higher magnification of the box in (C) reveals that a subset of donor cells (arrows) in the adult brain associate with vascular structures. (EH) GFP+ ADSCs in the P7 rat hippocampus do not initiate a host immunological response as indicated by the absence of ED 1+ reactive microglia within the proximity of donor cells (arrow). ED 1+(EH, arrowhead) are present, but not closely associated with donor GFP ADSCs. Scale bar: AH=20 µm.

DETAILED DESCRIPTION OF THE INVENTION

The present invention provides stem cells from the amnion. One aspect of the invention provides a method for obtaining an amnion-derived stem cell (ADSC) comprising: a. separating an amniotic membrane tissue sample from chorion of a mammalian embryo; b. culturing the amniotic membrane tissue sample; c. preparing a single-cell culture of ADSC isolated from the amniotic membrane tissue sample; d. culturing the ADSC; and e. obtaining or isolating the ADSCs. In one embodiment the amniotic membrane tissue sample is washed and fragmented after step a. and before step b. In one embodiment amniotic membrane tissue sample is cultured in Dulbecco's modified Eagle's medium (DMEM) supplemented with 20% fetal bovine serum (FBS).

The present invention relates to stem cells from the amnion, preferably the amniotic membrane. As used herein, the term "stem cell" refers to a master cell that can reproduce indefinitely to form the specialized cells of tissues and organs. A stem cell can divide to produce two daughter stem cells, or one daughter stem cell and one progenitor ("transit") cell, which then proliferates into the tissue's mature, fully formed cells. As used herein, the term "stem cell" includes multipotent and pluripotent stem cells.

As used herein, the term "pluripotent cell" refers to a cell that has complete differentiation versatility, i.e., the capacity to grow into any of the mammalian body's cell types, except for the extraembryonic tissues. A pluripotent cell can be self-renewing, and can remain dormant or quiescent within a tissue.

As used herein, the term "multipotent cell" refers to a cell that has the capacity to grow into two or more different cell types of the mammalian body within a given tissue or organ. However, a multipotent cell may have the capacity to be pluripotent. For example, hematopoietic stem cells were originally believed to be multipotent cells, i.e., stem cells that could develop into several types of blood cells, but not into brain cells. However, as discussed above, recent evidence suggests that hematopoietic stem cells may be pluripotent because they may differentiate into other types of cells, including brain cells.

As used herein, the term "progenitor cell" refers to a cell that is committed to differentiate into a specific type of cell or to form a specific type of tissue.

As used herein, the term "amnion" refers to a membranous sac which surrounds and protects the embryo. It is developed in reptiles, birds, and mammals. The primary function of this is the protection of the embryo for its future development into a fetus and eventually an animal. The amnion is the inner of the two fetal membranes surrounding the fetus (the chorion is the outer one). The terms "amnion", "amniotic membrane", and "amniotic tissue" are all used interchangeably in the present application. The amnion may be obtained from any reptilian, avian or mammalian species, including rodents, human, non-human primates, equines, canines, felines, bovines, porcines, ovines, lagomorphs, and the like. In one embodiment, the amnion is obtained from mouse, rat, or human.

In one embodiment the single-cell culture is prepared by enzymatically digesting the amniotic membrane tissue sample.

In one embodiment the ADSC is multipotent. In one embodiment the ADSC is pluripotent.

In one aspect the invention provides a multipotent ADSC obtained by the method of the present invention.

In one aspect the invention provides a pluripotent ADSC obtained by the method of the present invention.

An ADSC may be characterized by its cell markers. A variety of cell markers are known. See e.g., Stem Cells: Scientific Progress and Future Research Directions. Department of Health and Human Services. June 2001. http://www.nih.gov/news/stemcell/scireport.htm. Cell markers may be detected by methods known in the art, such as by immunochemistry or flow cytometry. Flow cytometry allows the rapid measurement of light scatter and fluorescence emission produced by suitably illuminated cells or particles. The cells or particles produce signals when they pass individually through a beam of light. Each particle or cell is measured separately and the output represents cumulative individual cytometric characteristics. Antibodies specific to a cell marker may be labeled with a fluorochrome so that it may be detected by the flow cytometer. See, eg., Bonner et al., Rev. Sci. Instrum 43: 404-409, 1972; Herzenberg et al., Immunol. Today 21: 383-390, 2000; Julius et al., PNAS 69: 1934-1938, 1972; Ormerod (ed.), Flow Cytometry: A Practical Approach, Oxford Univ. Press, 1997; Jaroszeski et al. (eds.), Flow Cytometry Protocols in Methods in Molecular Biology No. 91, Humana Press, 1997; Practical Flow Cytometry, 3.sup.rd ed., Wiley-Liss, 1995.

In one aspect the invention provides an isolated ADSC having at least one of the following characteristics: a. positive for cell markers CD29 and CD90; and b. negative for cell markers CD45 and CD11b. In one embodiment the ADSC has the following characteristics: a. positive for cell markers CD29 and CD90; and b. negative for cell markers CD45 and CD 11b.

In one aspect the invention provides an isolated ADSC which expresses at least one of the genes selected from the group consisting of Telomerase, Nanog, Sox2, □-III-Tubulin, NF-M, MAP2, APP, GLUT, NCAM, NeuroD, Nurrl, GFAP, NG2, Olig1, Alkaline Phosphatase, Vimentin, Osteonectin, Osteoprotegrin, Osterix, Adipsin, Erythropoietin, SM22-α, HGF, c-MET, α-1-Antriptrypsin, Ceruloplasmin, AFP, PEPCK 1, BDNF, NT-4/5, TrkA, BMP2, BMP4, FGF2, FGF4, PDGF, PGF, TGFα, TGFβ, and VEGF.

In one embodiment the ADSC expresses Telomerase, Nanog, Sox2, β-III-Tubulin, NF-M, MAP2, APP, GLUT, NCAM, NeuroD, Nuff 1, GFAP, NG2, Olig1, Alkaline Phosphatase, Vimentin, Osteonectin, Osteoprotegrin, Osterix, Adipsin, Elythropoietin, SM22-α, HGF, c-MET, α-1-Antriptrypsin, Ceruloplasmin, AFP, PEPCK 1, BDNF, NT-4/5, TrkA, BMP2, BMP4, FGF2, FGF4, PDGF, PGF, TGFα, TGFβ, and VEGF.

In one aspect the invention provides a composition comprising an ADSC of the present invention.

The present invention also embodies a homogeneous population of ADSCs.

As used herein, "homogeneous population" refers to a population of cells exhibiting substantially the same phenotype, such as that determined by cell markers. A homogeneous population may comprise at least about 70% of substantially the same cells, or at least about 80%, 90%, 92%, 96%, or 99% of substantially the same cells.

The present invention therefore provides a method of obtaining an ADSC by isolating amniotic cells having certain cell characteristics. The amniotic cells having these cell characteristics may be isolated from a single-cell culture of amniotic cells obtained from amniotic membrane as described above or from amniotic cells that have been cultured after isolating from the amniotic membrane. Cells may be isolated according to cell characteristics by, for example, flow cytometry, as described above.

In an embodiment of the present invention, ADSCs are isolated by isolating amniotic cells having at least one of the following characteristics: a. positive for cell markers CD29 and CD90; and b. negative for cell markers CD45 and CD1 lb. In one embodiment ADSCs are isolated by isolating amniotic cells having the following characteristics: a. positive for cell markers CD29 and CD90; and b. negative for cell markers CD45 and CD 11b.

In one embodiment ADSCs are isolated by isolating amniotic cells which express at least one of the genes selected from the group consisting of Telomerase, Nanog, Sox2, β-III-Tubulin, NF-M, MAP2, APP, GLUT, NCAM, NeuroD, Nuff 1, GFAP, NG2, Olig1, Alkaline Phosphatase, Vimentin, Osteonectin, Osteoprotegrin, Osterix, Adipsin, Erythropoietin, SM22-α, HGF, c-MET, α-1-Antriptrypsin, Ceruloplasmin, APP, PEPCK1, BDNF, NT-4/5, TrkA, BMP2, BMP4, FGF2, FGF4, PDGF, PGF, TGFα, TGFβ, and VEGF. In one embodiment ADSCs are isolated by isolating amniotic cells which express Telomerase, Nanog, Sox2, β-III-Tubulin, NF-M, MAP2, APP, GLUT, NCAM, NeuroD, Nurr1, GFAP, NG2, Olig1, Alkaline Phosphatase, Vimentin, Osteonectin, Osteoprotegrin, Osterix, Adipsin, Erythropoietin, SM22-α, HGF, c-MET, α-1-Antriptrypsin, Ceruloplasmin, APP, PEPCK 1, BDNF, NT-4/5, TrkA, BMP2, BMP4, FGF2, FGF4, PDGF, PGF, TGFα, TGFβ, and VEGF.

The present invention also provides a method for obtaining an ADSC. The method comprises a. separating an amniotic membrane tissue sample from chorion of a mammalian embryo; b. culturing the amniotic membrane tissue sample; c. preparing a single-cell culture of ADSC isolated from the amniotic membrane tissue sample; d. culturing the ADSC; and e. obtaining or isolating the ADSCs. In one embodiment the amniotic membrane tissue sample is washed and fragmented after step a. and before step b. In one embodiment amniotic membrane tissue sample is cultured in Dulbecco's modified Eagle's medium (DMEM) supplemented with 20% fetal bovine serum (PBS). Post-partum amnion may be obtained, for example, with informed consent from a caesarian procedure or normal birth. The amnion may be mechanically cut into smaller pieces of tissue, for example, with scissors. Before culturing the amniotic membrane, the membrane may be enzymatically digested with, for example, trypsin, chymotrypsin, lysozyme, amylase, or protease K. The amniotic cells thus obtained may be cultured in culture medium comprising standard medium, such as DMEM (Gibco) and 20% fetal bovine serum, and may be supplemented with glucose and/or antibiotics, as appropriate. ADSCs may be obtained by continued culture of the amniotic membrane in the culture medium.

The ADSCs of the present invention may also be induced into other cell types by methods known in the art.

The presence of ADSCs in culture may be detected by their ability to differentiate into different cell types. For example, the cultured cells may be tested for their ability to undergo neuronal, adipogenic, hepatic, and/or osteogenic differentiation.

In one aspect the invention provides a method for neurogenic differentiation of ADSCs, comprising culturing the ADSCs in a medium comprising an effective amount DMEM pH 7.0 (low glucose) buffered with 2.75 g/liter sodium bicarbonate and 5.96 g/liter HEPES (no serum), 2 mM Valproic Acid, 15 mM Betaine, 2.5 mM Taurine, 175 µM butylated hydroxyanisole, 27 nM selenium, 20 nM progesterone, 10 µM forskolin, 10 nM K252a, 5 Units/ml Heparin, 5 µg/ml Insulin, 1 mM sodium pyruvate, 50 mM □-thioglycerol, and 20 nM Bathocuproinedisulfonic acid, the medium supplemented with 10 ng/ml FGF2 every 48 hours, for about 2 to about 4 weeks to obtain a population of cells having at least one characteristic of a neural cell.

In one aspect the invention provides a method for osteogenic differentiation of ADSCs, comprising a. culturing the ADSCs in a medium comprising an effective amount of DMEM pH 7.4 (High glucose) supplemented with 100 nM Dexamethasone, 10 mM β-glycerol phosphate, 50 µM L-ascorbic acid-2-phosphate for about 2 to about 4 weeks; and b. obtaining a population of cells having at least one characteristic of a bone cell. Osteogenic differentiation may be induced by other methods known in the art.

Osteogenic differentiation may be detected by testing for the presence of osteogenic markers, which include, but are not limited to, osteopontin (OP), osteocalcin (OC), osteonectin (ON), and bone sialoprotein. Osteogenesis may also be detected by using von Kossa stain (Jaiswal et al., J Cell Biochem. 64: 295-312, 1997) and/or alizarin red stain (Wan et al., Chin. J. Traumatol. 5: 374-379, 2002), which detect the presence of calcium deposit activity. Neuronal differentiation may be induced by other methods known in the art.

Neuronal differentiation may be detected by testing for the presence of markers of neuronal and glial differentiation would include Nestin, Neurogenin-2 (Ngn-2), Musashi-1, Microtubule Dendrite Associated Protein-2 (MAP-2), Neurofilament-3 (NF-3), Synaptophysin (SYP), Tyrosine Hydroxylase (TH), Tryptophan Hydroxylase 2 (TPH2), Myelin Basic Protein (MBP), and Glial Fibrillary Acidic Protein (GFAP).

In one aspect the invention provides a method for adipose differentiation of ADSCs, comprising a. culturing the ADSCs in a medium comprising an effective amount of 10% FBS/DMEM, 500 µM IBMX, 1 µM dexamethazone stock, 5 µg/mL insulin and 50 µM indomethacin for about 3 days; b. culturing the ADSCs in a medium comprising an effective amount of 10% FBS/DMEM and 5 mg/mL insulin for about 3 days; c. repeating steps a. and b. in order 0 to about 5 times; and d. obtaining a population of cells having at least one characteristic of an adipocyte. Adipogenic differentiation may be induced by other methods known in the art.

Adipogenic differentiation may be detected by testing for the presence of adipogenic transcription factors PPARy2 (peroxisome proliferator activated receptor gamma) and/or CEBPa (CCAAT/enhancer binding protein alpha), by methods such as immunohistochemistry and reverse-transcriptase polymerase chain reaction. Alternatively, adipogenic differentiation may be detected by lipid accumulation as demonstrated by Oil Red O staining after culture in an adipocyte-inducing medium (Conget and Minguell, J. Cellular Physiology 181: 67-73, 1999). Other methods of inducing and detecting adipogenic differentiation may be used (see, e.g., Pittenger et al., Science 284: 143-147, 1999; Tchoukalova et al., Obesity Research 8: 664-672, 2000).

In one aspect the invention provides a method for hepatic differentiation of ADSCs, comprising culturing the ADSCs in a medium comprising an effective amount of 1% FBS/DMEM-LG, 20 ng/ml HGF, 10 ng/ml oncostatin M and 10 ng/ml FGF-4 for about 2 to about 4 weeks to obtain a population of cells having at least one characteristic of a hepatic cell. Hepatic differentiation may be induced by other methods known in the art.

Hepatic differentiation may be detected by testing for the presence of hepatocyte genes such as albumin (Alb) and alpha-1-antitrypsin (A1AT), and the transcription factor, C/EBPa. To confirm expression of prototypical liver genes, hepatically differentiated ADSCs can be immunostained with anti-serum albumin antibody and anti-hepatocyte nuclear factor (HNF)-4a antibodies.

In one aspect the invention provides a method for endothelial differentiation of ADSCs, comprising culturing the ADSCs in a medium comprising an effective amount of EGMTM-MV (catalog #CC-3125, from Cambrex) containing heparin, bovine brain extract, epithelial growth factor (e.g., human recombinant epithelial growth factor), and hydrocortisone for about 2 to about 4 weeks to obtain a population of cells having at least one characteristic of an endothelial cell. Endothelial differentiation may be induced by other methods known in the art.

Endothelial differentiation may be detected by testing for the presence of endothelial genes such as E-selectin (CD62E), ICAM-2 (CD102), CD34, and STRO-1.

In one aspect the invention provides a method of treating a patient comprising administering to the patient a therapeutically effective amount of an ADSC of the present invention and/or an ADSC which has differentiated into a particular progenitor cell or fully differentiated cell type. In the method of the present invention, the ADSCs and differentiated cells are transplanted into a subject in need of treatment in an amount effective to treat the nervous tissue degeneration. As used herein, the phrase "therapeutically effective amount" means effective to ameliorate or minimize the clinical impairment or symptoms of the disease or injury. For example, in the case of a neurodegenerative disease, the clinical impairment or symptoms of the neurodegenerative disease may be ameliorated or minimized by alleviating vasomotor symptoms, increasing deep-tendon reflexes, reducing muscle atrophy, restoring sensory function, and strengthening muscles. The amount of ADSCs and/or differentiated neural cells effective to treat disease or injury in a subject in need of treatment will vary depending upon the particular factors of each case, including the type of tissue, the stage of the disease or injury, the subject's weight, the severity of the subject's condition, the type of differentiated cells, and the method of transplantation. This amount may be readily determined by the skilled artisan, based upon known procedures, including clinical trials, and methods disclosed herein.

A patient is hereby defined as any person or non-human animal in need of treatment with an ADSC, or to any subject for whom treatment may be beneficial, including humans and non-human animals. Such non-human animals to be treated include all domesticated and feral mammals.

In an embodiment of the present invention, the ADSC to be administered is obtained from the same species as the species receiving treatment. Examples of mammalian species include rodents, human, non-human primates, equines, canines, felines, bovines, porcines, ovines, lagomorphs, and the like.

The ADSCs of the invention may be used in the treatment of any kind of injury due to trauma where tissues need to be replaced or regenerated. Examples of such trauma-related conditions include central nervous system (CNS) injuries, including injuries to the brain, spinal cord, or tissue surrounding the CNS injuries to the peripheral nervous system (PNS), or injuries to any other part of the body. Such trauma may be caused by accident, or may be a normal or abnormal outcome of a medical procedure such as surgery or angioplasty. The trauma may be related to a rupture or occlusion of a blood vessel, for example, in stroke or phlebitis. In specific embodiments, the cells may be used in autologous or heterologous tissue replacement or regeneration therapies or protocols, including, but not limited to treatment of corneal epithelial defects, cartilage repair, facial dermabrasion, mucosal membranes, tympanic membranes, intestinal linings, neurological structures (e.g., retina, auditory neurons in basilar membrane, olfactory neurons in olfactory epithelium), burn and wound repair for traumatic injuries of the skin, or for reconstruction of other damaged or diseased organs or tissues. Injuries may be due to specific conditions and disorders including, but not limited to, myocardial infarction, seizure disorder, multiple sclerosis, stroke, hypotension, cardiac arrest, ischemia, inflammation, age-related loss of cognitive function, radiation damage, cerebral palsy, neurodegenerative disease, Alzheimer's disease, Parkinson's disease, Leigh disease, AIDS dementia, memory loss, amyotrophic lateral sclerosis (ALS), ischemic renal disease, brain or spinal cord trauma, heart-lung bypass, glaucoma, retinal ischemia, retinal trauma, inborn errors of metabolism, adrenoleukodystrophy, cystic fibrosis, glycogen storage disease, hypothyroidism, sickle cell anemia, Pearson syndrome, Pompe's disease, phenylketonuria (PKU), porphyrias, maple syrup urine disease, homocystinmia, mucoplysaccharide nosis, chronic granulomatous disease and tyrosinemia, Tay-Sachs disease, cancer, tumors or other pathological or neoplastic conditions.

The ADSC used in the treatment may also contain a nucleic acid vector or biological vector in an amount sufficient to direct the expression of a desired gene(s) in a patient. The construction and expression of conventional recombinant nucleic acid vectors is well known in the art and includes those techniques contained in Sambrook et al., Molecular Cloning: A Laboratory Manual, Vols 1-3 (2d ed. 1989), Cold Spring Harbor Laboratory Press. Such nucleic acid vectors may be contained in a biological vector such as viruses and bacteria, preferably in a non-pathogenic or attenuated microorganism, including attenuated viruses, bacteria, parasites, and virus-like particles.

The nucleic acid vector or biological vector may be introduced into the cells by an ex vivo gene therapy protocol, which comprises excising cells or tissues from a patient, introducing the nucleic acid vector or biological vector into the excised cells or tissues, and reimplanting the cells or tissues into the patient (see, for example, Knoell et al., Am. J. Health Syst. Pharm. 55: 899-904, 1998; Raymon et al., Exp. Neurol. 144: 82-91, 1997; Culver et al., Hum. Gene Ther. 1: 399-410, 1990; Kasid et al., Proc. Natl. Acad. Sci. U.S.A. 87: 473-477, 1990). The nucleic acid vector or biological vector may be introduced into excised cells or tissues by, for example, calcium phosphate-mediated transfection (Wigler et al., Cell 14: 725, 1978; Corsaro and Pearson, Somatic Cell Genetics 7: 603, 1981; Graham and Van der Eb, Virology 52: 456, 1973). Other techniques for introducing nucleic acid vectors into host cells, such as electroporation (Neumann et al., EMBO J. 1: 841-845, 1982), may also be used.

The cells of the invention may also be co-administered with other agents, such as other cell types, growth factors, and antibiotics. Other agents may be determined by those of ordinary skill in the art.

In one aspect the invention provides a method of treating a neurodegenerative disease or a brain or spinal cord injury in a patient, wherein the method comprises administering a therapeutically effective amount of an ADSC of the present invention or a population of neurogenically differentiated cell of the present invention to a patient having a neurodegenerative disease or a brain or spinal cord injury. In one embodiment the neurodegenerative disease is selected from the group consisting of Parkinson's disease, Alzheimer's disease, Pick's disease, Huntington's disease, spingolipidoses, mucosaccharidoses, and amyotrophic lateral sclerosis.

In one aspect the invention provides a method of treating a bone disease in a patient, wherein the method comprises administering a therapeutically effective amount of an ADSC of the present invention or the population of osteogenically differentiated cells of the present invention to a patient having the bone disease. In one embodiment the bone disease is selected from the group consisting of osteoporosis, Paget's disease, osteogenesis imperfecta, and osteoarthritis.

In one aspect the invention provides a method of treating a hepatic disease in a patient, wherein the method comprises administering a therapeutically effective amount of an ADSC of the present invention or the population of hepatically differentiated cells of the present invention to a patient having the hepatic disease. In one embodiment the hepatic disease is selected from the group consisting of amebic liver abscess, autoimmune hepatitis, biliary atresia, cirrhosis, coccidioidomycosis; disseminated, delta agent (Hepatitis D), drug-induced cholestasis, hemochromatosis, hepatitis A, hepatitis B, hepatitis C, hepatocellular carcinoma, liver cancer, liver disease due to alcohol, primary biliary cirrhosis, pyogenic liver abscess, Reye's syndrome, sclerosing cholangitis, and Wilson's disease.

In one aspect the invention provides a method of treating a cardiovascular disease in a patient, wherein the method comprises administering a therapeutically effective amount of an ADSC of the present invention to a patient having the cardiovascular disease. In one embodiment the cardiovascular disease is selected from the group consisting of congenital heart defects, peripheral artery disease, arterio-arterial fistula, arteriovenous fistula, cerebral arteriovenous malformations, aortic coarctation, cor triatum, coronary vessel anomalies, patent ductus arteriosus, Ebstein's anomaly, hypoplastic left heart syndrome, levocardia, transposition of great vessels, double outlet right ventricle, tricuspid atresia, persistent truncus arteriosus, and heart septal defects, such as aortopulmonary septal defect, endocardial cushion defects, Lutembacher's Syndrome, ventricular heart septal defects, cardiac tamponade, endocarditis (including bacterial), heart aneurysm, cardiac arrest, congestive heart failure, congestive cardiomyopathy, paroxysmal dyspnea, cardiac edema, post-infarction healt rupture, ventricular septal rupture, heart valve diseases, myocardial diseases, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, cardiovascular syphilis, cardiovascular tuberculosis, anhythmias such as sinus arrhythmia, atrial fiblillation, atrial flutter, bradycardia, extrasystole, Adams-Stokes Syndrome, bundle-branch block, sinoatrial block, long QT syndrome, parasystole, sick sinus syndrome, ventricular fibrillations, tachycardias such as paroxysmal tachycardia, supraventricular tachycardia, accelerated idioventlicular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia and heart valve diseases such as aortic valve insufficiency, aortic valve stenosis, heart murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

In one aspect the invention provides a method of treating a metabolic disease in a patient, wherein the method comprises administering a therapeutically effective amount of an ADSC of the present invention to a patient having the metabolic disease. In one embodiment the metabolic disease is selected from the group consisting of Phenylketonuria, Alkaptonmia, Ochronosis, Tyrosinemia, Albinism, Histidinemia, Maple syrup urine disease, Propionic acidemia, Methylmalonic acidemia, Isovaleric acidemia, 3-Methylcrotonyl-CoA carboxylase deficiency, Cystinuria, Cystinosis, Hartnup disease, Homocystinuria, Cystathioninuria, N-cetylglutamate synthase deficiency, Carbamoyl phosphate synthetase I deficiency, Ornithine transcarbamylase deficiency, Citrullinemia, Argininosuccinic aciduria, Hyperammonemia, Glutaric acidemia type 1, Sarcosinemia, Lactose intolerance, type I Glycogen storage disease, type II Glycogen storage disease, type III Glycogen storage disease, type IV Glycogen storage disease, type V Glycogen storage disease, type VI Glycogen storage disease, type VII Glycogen storage disease, Fructose intolerance, Essential fructosuria, Galactosemia, PCD, PDHA, Pentosuria, Renal glycosuria, GM2 gangliosidoses, Sandhoff disease, Tay-Sachs disease, GM1 gangliosidoses, Mucolipidosis type IV, Gaucher's disease, Niemann-Pick disease, Farber disease, Fabry's disease, Metachromatic leukodystrophy, Krabbe disease, Neuronal ceroid lipofuscinosis, Batten disease, Cerebrotendineous xanthomatosis, Cholesteryl ester storage disease, Wolman disease, Hyperlipidemia, Hypercholesterolemia, Familial hypercholesterolemia, Xanthoma, Combined hyperlipidemia, Lecithin cholesterol acyltransferase deficiency, Tangier disease, Abetalipoproteinemia, Adrenoleukodystrophy, primary camitine deficiency, carnitine palmitoyltransferase I deficiency, camitine palmitoyltransferase II deficiency, camitine-acylcamitine translocase deficiency, Wilson's disease, Menkes disease, Haemochromatosis, Acrodermatitis enteropathica, Hypophosphatemia, Hypophosphatasia, Hypermagnesemia, Hypomagnesemia, Hypercalcaemia, Hypocalcaemia, Disorders of calcium metabolism, Hyperuricemia, Lesch-Nyhan syndrome, Xanthinuria, Gilbert's syndrome, Crigler-Najjar syndrome, Dubin-Johnson syndrome, Rotor syndrome, Mucopolysaccharidosis, Hurler Syndrome, Hunter Syndrome, Sanfilippo Syndrome, Morquio Syndrome, Maroteaux-Lamy Syndrome, Sly Syndrome, Mucolipidosis, I-cell disease, Pseudo-Hurler polydystrophy, Aspartylglucosaminuria, Fucosidosis, Alpha-mannosidosis, Sialidosis, Alpha 1-antitrypsin deficiency, Cystic fibrosis, Amyloidosis, Familial Mediterranean fever, and Acatalasia.

In one embodiment of the present invention, the ADSCs are useful for inducing new blood vessel formation in a patient. New blood vessels can be formed by vasculogenesis (formation of blood vessels from embryonic precursors), angiogenesis (in-growth of blood vessels from the surrounding tissue) or the formation of neovascularization (formation of new blood vessels where they had not been previously) including forming blood vessels from endothelial progenitor cells linking to existing blood vessels. There are numerous conditions in which a mammal may be in need of forming new blood vessels such as injury due to trauma, surgery or acute or chronic diseases. For example, the mammal may have a wound that requires healing. In another non-limiting example, the patient may have undergone cardiovascular surgery, cardiovascular angioplasty, carotid angioplasty, or coronary angioplasty, which are all conditions requiring new blood vessel formation. In another non-limiting example, patients who have had a myocardial infarction, such as an aMI, are in need of new blood vessel formation. Other conditions which may require new blood vessel formation include sickle cell anemia and thalassemia.

In another embodiment of the present invention, the ADSCs can be administered to the mammal in need of forming new blood vessels by any route or method that allows the preferential migration of the cells to the site in need of new blood vessel formation. Exemplary routes of administration include, but are not limited to, systemic administration such as intravenous injection, localized implantation such as localized intramuscular or subcutaneous injection of the progenitor cells in biocompatible solutions or biodegradable biocompatible matrices. Biocompatible solutions are known to those skilled in the art. Examples of biodegradable biocompatible matrices include, but are not limited to, solubilized basement membrane, autologous platelet gel, collagen gels or collagenous substrates based on elastin, fibronectin, laminin, extracellular matrix and fibrillar proteins.

The present invention further provides a composition comprising an ADSC of the invention. The present invention also provides a pharmaceutical composition comprising an ADSC of the invention. The ADSC of the invention or formulations thereof may be administered by any conventional method including parenteral (e.g. subcutaneous or intramuscular) injection or intravenous infusion. The treatment may consist of a single dose or a plurality of doses over a period of time. The pharmaceutical composition may comprise one or more acceptable carriers. The carrier(s) must be "acceptable" in the sense of being compatible with the ADSC and not deleterious to the recipients thereof. Typically, the carriers may be water or saline which will be sterile and pyrogen free.

In one aspect the invention provides a cryopreserved ADSC of the present invention.

In one embodiment the invention provides a method of cryopreserving ADSCs comprising: a. washing a population of ADSCs; b. suspending the population of ADSCs in a cryopreservation medium comprising 60% Dulbecco's Modified Eagles Media (DMEM)/30% Fetal Bovine Serum (PBS)/10% Dimethyl sulfoxide (DMSO); and c. storing the population at a temperature below about −80° C.

In one embodiment the invention provides a method of cryopreserving ADSCs comprising: a. washing a population of ADSCs; b. suspending the population of ADSCs in a cryopreservation medium comprising 60% DMEM/30% Liforcel serum substitute/10% DMSO; and c. storing the population at a temperature below about −80° C.

In one aspect the invention provides a cryopreserved amniotic membrane tissue sample. In one aspect the invention provides a method of cryopreserving an amniotic membrane explant, which allows for the future isolation of ADSC populations. Freshly isolated amniotic membrane tissue can be cryopreserved intact (without the need for cell dissociation) in liquid nitrogen or in a standard −80° C. laboratory freezer indefinitely. When retrieved from cryopreservation and placed into culture, viable stem cell populations are readily established. This methodology 1) minimizes handling requirements at the time of amnion isolation, 2) decreases costs associated with long-term cryopreservation (freezer storage) and 3) allows for simple and reliable establishment of stem cell cultures for propagation and manipulation. This methodology may be adaptable to other solid tissues and associated stem cells.

In one embodiment the invention provides a method of cryopreserving a amniotic membrane tissue sample comprising: a. washing the amniotic membrane tissue sample; b. suspending the amniotic membrane tissue sample in a cryopreservation medium comprising 60% Dulbecco's Modified Eagles Media (DMEM)/30% Fetal Bovine Serum (PBS)/10% Dimethyl sulfoxide (DMSO); and c. storing the population at a temperature below about −80° C.

In one embodiment the invention provides a method of cryopreserving an amniotic membrane tissue sample comprising: a. washing the amniotic membrane tissue sample; b. suspending the amniotic membrane tissue sample in a cryopreservation medium comprising 60% DMEM/30% Liforcel serum substitute/10% DMSO; and c. storing the population at a temperature below about −80° C.

Other than in the operating examples, or where otherwise indicated, all numbers expressing quantities of ingredients, reaction conditions, and so forth used in this application are to be understood as being modified in all instances by the term "about." Accordingly, unless the contrary is indicated, the numerical parameters set forth in this application are approximations that may vary depending upon the desired properties sought to be obtained by the present invention. At the very least, and not as an attempt to limit the application of the doctrine of equivalents to the scope of the claims, each numerical parameter should be construed in light of the number of reported significant digits and by applying ordinary rounding techniques.

Notwithstanding that the numerical ranges and parameters setting folth the broad scope of the invention are approximations, the numerical values set forth in the specific examples are reported as precisely as possible. Any numerical value, however, inherently contains certain errors necessarily resulting from the standard deviation found in the respective testing measurements.

It must be noted that as used herein and in the appended claims, the singular forms "a", "and", and "the" include plural referents unless the context clearly dictates otherwise.

Unless defined otherwise, all technical and scientific terms used herein have the same meaning as commonly understood by one of ordinary skill in the art to which this invention belongs. Although any methods and materials similar or equivalent to those described herein can also be used in the practice of the present invention, exemplary methods and materials are described for illustrative purposes.

All publications mentioned in this application are incorporated by reference to disclose and describe the methods and/or materials in connection with which the publications are cited. Additionally, the publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Methods, techniques, and/or protocols (collectively "methods") that can be used in the practice of the invention are not limited to the particular examples of these procedures cited throughout the specification but embrace any procedure known in the art for the same purpose. Furthermore, although some methods may be described in a particular context in the specification, their use in the instant invention is not limited to that context.

The specification is most thoroughly understood in light of the teachings of the references cited within the specification, all of which are hereby incorporated by reference in their entirety. The embodiments within the specification provide an illustration of embodiments of the invention and should not be construed to limit the scope of the invention. The skilled artisan recognizes that many other embodiments are encompassed by the claimed invention and that it is intended that the specification and examples be considered as exemplary only, with the true scope and spirit of the invention being indicated by the following claims.

The present invention is illustrated by the following Examples, which are not intended to be limiting in any way.

EXAMPLES

Example 1—Methods

ADSC Isolation, Culture and Cloning

Rat amnion membrane is mechanically separated from the chorion of embryonic day 18.5 (E18.5) Sprague-Dawley rat embryos. The tissue is washed extensively with phosphate buffered saline (PBS) and subsequently cut into small pieces. Membrane fragments are placed in 6-well plastic tissue culture dishes in a minimal volume (0.5 ml) of Dulbecco's modified Eagle's medium [DMEM; Invitrogen, Carlsbad, Calif.] supplemented with 20% Fetal Bovine Serum [PBS; Atlanta Biologicals, Atlanta, Ga.] to encourage attachment. Cells begin to emerge from the explanted tissues within 24 hours of plating. After one week the tissue explants are removed and the remaining adherent cells are trypsinized and re-plated into 100 mm plastic culture dishes. Cultures are passaged at confluency. All cultures are maintained under a humidified atmosphere of 5% $CO_2$ at 37° C. ADSCs used in these studies are extensively propagated up to 50 passages in vitro.

Generation of Clonal Lines

Clonal lines are generated from single cells as previously described (Black and Woodbury, 2001). Briefly, ADSCs are plated at a density of 1 cell/$cm^2$ in 150 mm plastic culture dishes and incubated for 2 hours to allow cell attachment. Supernatant is removed and dishes are washed with PBS to eliminate unattached cells. Dishes are examined microscopically and isolated single cells are identified and marked. Colonies arising from these single cells are then expanded into clonal lines.

Flow Cytometry

ADSC parent and clonal cultures are trypsinized and suspended in 20% FBS/DMEM. Samples are centifuged and suspended in PBS. $1 \times 10^6$ cells are placed into separate 1.5 ml tubes, washed 2× with PBS and incubated for 1 hour at room temperature with the following FITC-conjugated primary antibodies [Becton Dickinson, Franklin Lakes, N.J.]: CD11b (rat, 1:500), CD44 (rat, 1:500), CD45 (rat, 1:500), CD29 (guinea pig, 1:500), CD90 (rat, 1:500) and PE-conjugated CD31 (rat, 1:200). Control samples are incubated in PBS without primary antibody. Cell suspensions are fixed with 4% paraformaldehyde (PFA) and analyzed by the Coulter Cytomics FC500 Flow Cytometer.

RNA Isolation

RNA is isolated from induced and control ADSCs using Trizol reagent according to manufacturer's recommendations [Life Technologies, Carlsbad, Calif.]. The resulting RNA pellet is subjected to a chloroform extraction and two ethanol precipitations.

cDNA Synthesis

2 μg of RNA are reverse-transcribed using Superscript II reverse transcriptase [Life Technologies] in a 20 μl volume containing 1 μg of oligo-dT primer, 200 μM dNTPs, and buffers supplied by the manufacturer. The reaction is carried out in a Perkin-Elmer 9600 polymerase chain reaction (PCR) machine with the following parameters: 25° C. 5 minutes, 37° C. 5 minutes, 42° C. 60 minutes, and 48° C. 10 minutes. A 5 minute ramp time is employed between each temperature. In control reactions the Superscript II reverse transcriptase is omitted. Polymerase Chain Reaction cDNA target (1 μl) is amplified by PCR using specific primer pairs (see Table 1). Sequences for telomerase primers are obtained from a previously published report (Ginis et al., 2004). PCR reactions employed Tfl polymerase and MasterAmp PCR Optimization Buffer [Epicentre, Madison, Wis.] according to manufacturer's recommendations. PCRs are performed in a Rapid Cycler 2 [Idaho Technologies, Salt Lake City, Utah] as follows: initial 2 minute denaturing step at 94° C. followed by 35-40 cycles of 94° C. 1 second, 52-60° C. 11 seconds, 72° C. 30-70 seconds. All reactions are performed in 10 μl volumes. Brain and liver tissue extracts are used as positive PCR controls.

TABLE 1

Primer Sequences

| Full Name | Abbreviated Name | Forward Primer 5'→3' | Forward Primer SEQ ID | Reverse primer 5'→3' | Reverse Primer SEQ ID NO |
|---|---|---|---|---|---|
| Telomerase | | CTGCGT GTGCGT GCTCTG GAC | 1 | CACCTC AGCAAA CAGCTT GTTCTC | 2 |

TABLE 1-continued

Primer Sequences

| Full Name | Abbreviated Name | Forward Primer 5'→3' | Forward Primer SEQ ID | Reverse primer 5'→3' | Reverse Primer SEQ ID NO |
|---|---|---|---|---|---|
| Nanog | | TGCTCTGCACAGAGACTGGTAAGC | 3 | TCTGGTTGCTCCAGGTTGGGTTGG | 4 |
| SRY-related HMG-boxgene 2 | Sox2 | ACATGATGGAGACGGAGCTGAAGC | 5 | GCTGCTCCTGCATCATGCTGTAGC | 6 |
| Neurogenic differentiation factor | NeuroD | TGACCAAATCATACAGCGAGAGC | 7 | AGAAGTTGCCATTGATGCTGAGCG | 8 |
| Orphan nuclear hormone receptor-I | Nurr-1 | CTCCCGGAGGAACTGCACTTCGGC | 9 | GTGTCTTCCTCTGCTCGATCATAT | 10 |
| Neural cell adhesion molecule | NCAM | TGCTCAAGTCCCTAGACTGGAACG | 11 | CTTCTCGGGCTCTGTCAGTGGTGTGG | 12 |
| NMDA glutamate binding subunit | GLUT | AGTTTCTTGGTCTCTGGGGACAGC | 13 | AACTGATGGTCAGGATCGACAGGG | 14 |
| β-III-Tubulin | | TGCTCATCAGCAAAGTGCGTGAGG | 15 | ATGGCCAGCATCTGCTCATCCACC | 16 |
| Neurofilament M | NF-M | CTCGACTTCAGCCAGTCCTCTTCG | 17 | TCTTTGCGCTCTACGGTGATGTGC | 18 |
| Microtubule associated protein-2 | MAP-2 | TAACCAACACTAGCGGAACGATGG | 19 | TACCTCTGGCACTGAACTGAGACC | 20 |
| Tau | | GGCTTTGAAGCAGCATGGCTGAAC | 21 | GGCCTGATCACAAACCCTGCTTGG | 22 |
| Growth associated protein 43 | GAP43 | ATGCTGTGCTGTATGAGAAGAACC | 23 | TCAGGCATGTTCTTGGTCAGCCTC | 24 |
| Amyloid precursor protein | APP | AGTTTCTTGGTCTCTGGGGACAGC | 25 | AACTGATGGTCAGGATCGACAGGG | 26 |
| Glial fibrillary acidic protein | GFAP | AGCTGAACCAGCTTCGAGCCAAGG | 27 | GGAAGCAACGTCTGTGAGGTCTGC | 28 |
| Membrane-spanning proteoglycan NG2 | NG-2 | TGGTAGCCCAGAAGCAGGTACTCC | 29 | TGTCCTGCAGTCAGCTCAGATTGC | 30 |

TABLE 1-continued

Primer Sequences

| Full Name | Abbreviated Name | Forward Primer 5'→3' | Forward Primer SEQ ID | Reverse primer 5'→3' | Reverse Primer SEQ ID NO |
|---|---|---|---|---|---|
| Tyrosine hydroxylase | TH | GACGGCGACAGAGTCTCATCGAGG | 31 | CAGCAGTCCGGCTCAGGTGAATGC | 32 |
| Alkaline Phosphatase | AP | AAGACCCCAGTTACTGGCGACAGC | 33 | CCTTTCCGATGGCCTCATCCATCT | 34 |
| Erythropoietin |  | CACCTCAGCAAACAGCTTGTTCTC | 35 | CAGAGTGACGGTGAGCGAGTTGGC | 36 |
| Fibronectin |  | F-GGAATGGACCTGCAAGCCAATAGC | 37 | R-GAATTCCCACCTCGAGTCTGAACC | 38 |
| Vimentin |  | CCAACGAGAAGGTGGAATTGCAGG | 39 | GCCATCTTTACATTGAGCAGGTCC | 40 |
| Osteonectin |  | CGGAAGCTGCAGAAGAGATGGTGG | 41 | TGTCCTGCTCCTTGATGCCAAAGC | 42 |
| Osteopontin |  | TCGGAGGAGAAGGCGCATTACAGC | 43 | TCCTCATGGCTGTGAAACTCGTGG | 44 |
| Osteoprotegrin |  | ACGAGTGATGAATGCGTGTACTGC | 45 | TCTCGTTCTCTCAATCTCGTCTGG | 46 |
| Osterix |  | CCTTCTCAAGCACCAATGGTCTCC | 47 | ACTGCCTGCATATCCACCACTGCC | 48 |
| Adipsin |  | CAGTGCAAGTGAATGGCACGCACG | 49 | TCAATCCACGGCACGTAGGTTGCC | 50 |
| Smooth protein 22-α, | SM22-α | TCTCCTTCCAGTCCACAAACGACC | 51 | CTTCCCTTTCTAACTGATGATCTG | 52 |
| Albumin |  | TCGTGACAACTACGGTGAACTGGC | 53 | TGTTCTGTCTCAGCGAGACACTGG | 54 |
| Glutamine synthetase | GS | CCCACTTGAACAAAGGCATCAAGC | 55 | GGTCCTATCTGGAATTCCCACTGG | 56 |
| Hepatocyte nuclear factor 3α | HNF-3α | GCAGGCTCCATGAACATGTCATCC | 57 | GCTGAACCTGAGAAGCCTGTGTCC | 58 |

TABLE 1-continued

Primer Sequences

| Full Name | Abbreviated Name | Forward Primer 5'→3' | Forward Primer SEQ ID | Reverse primer 5'→3' | Reverse Primer SEQ ID NO |
|---|---|---|---|---|---|
| Hepatocyte growth factor | HGF | CAAGCAATCCAGAGGTACGCTACG | 59 | GCACAGGATATTACAGGATGGTCC | 60 |
| Hepatocyte growth factor receptor | C-MET | CCCTAGTGAAGTCTGAGATGAACG | 61 | GGAATCTCGGAATTCTGGCAGGAC | 62 |
| α-1-antitrypsin | α-I-AT | GACAAGGCAGTTCCAGCATGCTGC | 63 | GCTGGCAGCACGTTGAGGCAATGC | 64 |
| Ceruloplasmin | | CTACAGTTGCTCCAACGTTGCCAGG | 65 | AGTAACCAGCTTCCAGGCGTTTGG | 66 |
| α-fetoprotein | AFP | GACAAGGCAGTTCCAGCATGCTGC | 67 | GCTGGCAGCACGTTGAGGCAATGC | 68 |
| Phosphoenolpyruvate carboxykinase-1 | PEP-CKI | CTCCTCAGCTGCATAATGGTCTGG | 69 | TGGGGTTCATCATGGCCAGGTTGG | 70 |
| Nerve growth factor | NGF | CCAAACTGGAGGAGATGATGCTGC | 71 | CAAAGTGTTGCCACTGTTGGGTGC | 72 |
| Neurotrophin-4/5 receptor kinase-A | NT-45 | TCCTCCTTTTCCTTCTCCTCCTCCGTGGCTGTCAAGGCACTGAAGG | 73 | GCACATAGGACTGTTTAGCCTTGCTGTTGGAGAGCTGGTACCAGG | 74 |
| Bone morphogenetic protein-2 | BMP2 | CTGTCTTUTAGTGTTGCTGCTTCC | 77 | TTCTGAGTCACTAACCTGGTGTCC | 78 |
| Bone morphogenetic protein-4 | BMP4 | ACACTGTGAGGAGTTTCCATCACG | 9 | TTCCAGCCCACGTCACTGAAGTCC | 80 |
| Transforming growth factor-α | TGFα | GTATCCTGGTAGCTGTGTGTCAGG | 81 | AGACCACTGTCTCAGAGTGGCAGC | 82 |
| Transforming growth factor-β | TGFβ | CCACCTGCAAGACCATCGACATGG | 83 | GGACTGATCCCATTGATTTCCACG | 84 |
| Vascular endothelial growth factor | VEGF | TTTCTGCTCTCTTGGGTGCACTGG | 85 | TGGCTTGTCACATCTGCAAGTACG | 86 |

TABLE 1-continued

Primer Sequences

| Full Name | Abbreviated Name | Forward Primer 5'→3' | Forward Primer SEQ ID | Reverse primer 5'→3' | Reverse Primer SEQ ID NO |
|---|---|---|---|---|---|
| Placental growth factor | PGF | CACTTGCTTCTTGCAGGTCCTAGC | 87 | TGCCTTTGTCGTCTCCAGAATAGG | 88 |
| Fibroblast growth factor-2 | FGF2 | AAGCGGCTCTACTGCAAGAACGGC | 89 | TCCGAGTTTATACTGCCCAGTTCG | 90 |
| Fibroblast growth factor-4 | FGF4 | GACTACCTGCTGGGCCTCAAAAGG | 91 | GGAAGTGGGTTACCTTCATGGTCG | 92 |
| Platelet derived factor | PDGF | AGCGACTGGCTCGAAGTCAGATCC | 93 | TCCAGGTGCTCCTCTAACCTCACC | 94 |
| Epidermal growth | EGF | CTGTACTCAGTGTCACAGCACAGC | 95 | CATAGTAAGCAAATCGTGCCGTGC | 96 |
| Glyceraldehyde 3-phosphatedehydrogenase | GAPDH | TGTGAACGGATTTGGCCGTATCGG | 97 | ATGCCAGTGAGCTTCCCGTTCAGC | 98 |

Immunocytochemistry

Cells are fixed in 4% PFA and stored in PBS at 4° C. until stained. Fixed cultures are blocked with 5% donor goat serum/0.3% Triton PBS for 45 minutes, followed by incubation in the following primary antibodies for 24 hours at 4° C.: fibronectin [(rabbit), 1:1000, Sigma], nestin [(rabbit), 1:200, Santa Cmz Biotechnologies, Santa Cruz, Calif.], vimentin [(mouse, rabbit), 1:250-1:500, Santa Cruz Biotechnologies], neurofilament-M [(mouse, rabbit), 1:250-1:500, Chemicon, Temecula, Calif.], and tau [(mouse), 1:250, Santa Cmz] After extensive washing, cultures are incubated at 37° C. for 60 minutes with the species-specific Alexa Fluor 594 or 488 [1:750, Molecular Probes, Eugene, Oreg.] secondary antibodies. Primary antibodies are omitted in all negative controls. 4,6-Diamidino-2-phenyindole (DAPI) [1 µg/mL, Sigma] is used as a nuclear counterstain. All samples are cover slipped with Fluoromount G [Electron Microscopy Systems, Fort Washington, Pa.] and visualized with an inverted fluorescent microscope [Zeiss Axiovert, Thomwood, N.Y.].

Neural Induction

Neuronal differentiation is performed as previously described (Kramer et al., 2006) with modification. The media is supplemented with 10 ng/ml bFGF at 24 hours post-induction and every 48 hours thereafter. Cells in neural induction media (NIM) are maintained under a humidified atmosphere of 5% $CO_2$ in air at 30° C. Neural differentiation is determined by morphological changes and immunocytochemical analysis. In addition, RT-PCR is performed on mRNA isolated from ADSCs cultured in NIM for 7 days, examining expression of neuralspecific genes.

Adipogenic Induction

Prior to adipogenic differentiation, ADSCs are rinsed extensively with PBS. ADSCs are exposed to an adipogenic induction media (AIM) consisting of 10% FBS/DMEM, 500 µM IBMX, 1 µM dexamethasone, 10 µg/mL insulin and 100 µM indomethacin. Following three days in the AIM, ADSCs are cultured in adipogenic maintenance media (AMM) for three days. AMM consisted of 10% FBS/DMEM and 10 µg/mL insulin in a base of DMEM. ADSCs are maintained at 37° C. for 3 weeks with media changed every third day. Cells are fixed with 4% PFA and stored at 4° C. until stained. Control cultures are grown in 10% FBS/DMEM. Oil Red 0 is utilized to visualize fat droplets.

Osteogenic Induction

Osteogenic differentiation is performed as described previously (Woodbury et al., 2002). ADSCs are maintained in osteogenic induction media up to 6 weeks with fresh media added every third day. Cells are fixed with 4% PFA and stored at 4° C. until stained. Control cultures are grown in 10% FBS/DMEM. Alizarin red is utilized to visualize mineralized matrix. RNA is obtained at 4 and 6 weeks post-induction and subjected to RT-PCR, examining expression of bone-specific genes.

Hepatogenic Induction

ADSCs are seeded onto fibronectin-coated dishes at a density of ~3,000 cell/$cm^2$ and grown to 70% confluency in serum containing media (SCM). Cultures are subsequently transferred to hepatocyte induction media (HIM) consisting of 20 ng/ml hepatocyte growth factor (HGF), 10 ng/ml oncostatin M (OSM), 10 ng/ml FGF-4, $10^{-8}$ M dexamethasone, 1% FBS in low glucose (LG) DMEM and maintained in this media until harvested. Control cultures are maintained in 1% FBS/LG-DMEM without additional factors. Media is changed every 3-4 days. Hepatic differentiation of the ADSCs is determined by DiI-Ac-LDL (low-density lipoprotein) uptake [Biomedical Technologies, Stoughton, Mass.] and Periodic Schiff Acid (PAS) staining for glycogen. RNA is obtained at 2 and 3 weeks posted induction and subjected to RT-PCR, examining expression of liver-specific genes.

Reporter Vector Construction and Transfection into ADSCs

The pEF1/eGFP vector used for transfection of ADSCs is generated from two commercially available vectors. The GFP expression vector is constructed from elements derived from two commercially available vectors. pEf1/myc/his (Invitrogen) containing the elongation factor 1 promoter (EF1) upstream of a multiple cloning site (MCS) serves as the vector backbone. The eGFP gene, isolated from pVivo2GFPLacZ (InvivoGen) is inserted into the MCS, allowing regulated expression by the EF1 promoter. The EF1GFP chimeric vector is introduced into proliferating ADSCs using Lipofectamine (Invitrogen) as recommended by the manufacturer. Stable transfectants are selected using G418. Clonal lines expressing high levels of GFP are identified via microscopic examination. For transplantation studies GFPADSC clone 2 is utilized, which demonstrates the stem cells characteristics of self-renewal and multi-differentiation in vitro. This clone uniformly expresses GFP and stable reporter gene expression is maintained at least 25 passages, the longest time examined.

Transuterine Intraventricular Injection

Timed pregnant rats, 15.5 days postcoitum (E15.5) serve as hosts. Animals are sedated by an i.p. injection of ketamine (50 mg/kg) xylazine (2.6 mg/kg) acepromazine (0.65 mg/kg). A 3 cm ventral midline incision exposes the abdominal cavity, revealing the uterine horns and enclosed embryos. Guided by fiber optic transillumination, 23 µl of ADSCs cell suspension (100,000-150,000 cells in total) are pressure-injected into the lateral ventricles of fetal brains using a glass capillary pipette. Successful injections are evidenced by rapid diffusion of the fast green dye throughout the ventricular system. Embryos that do not receive donor cells are sacrificed in utero by intraventricular infusion of 9% saline.

Tissue Processing

For prenatal time points, dams are euthanized, embryos are retrieved and brains are microdissected. Brain tissue is immersion-fixed in 4% paraformaldehyde (PFA) for 24 hours at 4° C., rinsed 3x with PBS, then fixed for an additional 24 hours in 30% sucrose/4% PFA. Tissue is then stored in 30% sucrose/PBS until processing.

Postnatal animals are euthanized by an injection of pentobarbital (0.5 ml, 50 mg/ml), perfused with saline, followed by 4% PFA. Brains are removed and postfixed in 4% PFA for 24 hours, and subsequently stored in 30% sucrose/PBS until they are sectioned. All samples are sagitally, coronally or horizontally cryosectioned at 16 tm, and processed immunohistochemically.

Immunohistochemistry and Microscopic Analysis.

Slides containing 16 µm sections are rinsed extensively with PBS. Slides are placed in citric acid buffer solution (pH 6.0), microwaved until boiling and allowed to cool slowly to ambient temperature. The microwave step is repeated three times for optimal antigen retrieval. Tissues are blocked with 5% donor goat serum for 45 minutes. Sections are subsequently incubated for 24 hours with primary antibodies: GFP [(mouse, rabbit), 1:250l:500, Chemicon], vimentin [(mouse, rabbit), 1:250l:500, Santa Cruz Biotechnologies], Nestin [(mouse), 1:250, DSHB], □-III tubulin [(mouse), 1:500, Chemicon], glial fibrillary acidic protein (GFAP) [(rabbit), 1:1000, Sigma], NeuN [(mouse), 1:250, Chemicon], adenomatous polyposis coli (APC) [(mouse), 1:200, Calbiochem] and von Willebrand factor (vWF) [(rabbit), 1:500, Chemicon]. After numerous washes, the sections are incubated with secondary antibodies: species specific Alexa Fluor 594 or 488 is used (1:500, Molecular Probes). 4,6Diamidino2phenyindole (DAPI) [1 µg/mL] or propidium iodide (PI) [20 ug/ml dH20] are used as a nuclear counterstains. Negative controls performed by omitting the primary antibody. All samples are cover slipped with Fluoromount G [Electron Microscopy Systems] and visualized with an inverted fluorescent microscope [Zeiss Axiovert]. Zsectioning is utilized to colocalize all cellular markers.

Example 2—Amnion-Derived Stem Cell Isolation and Characterization

Figure 1:
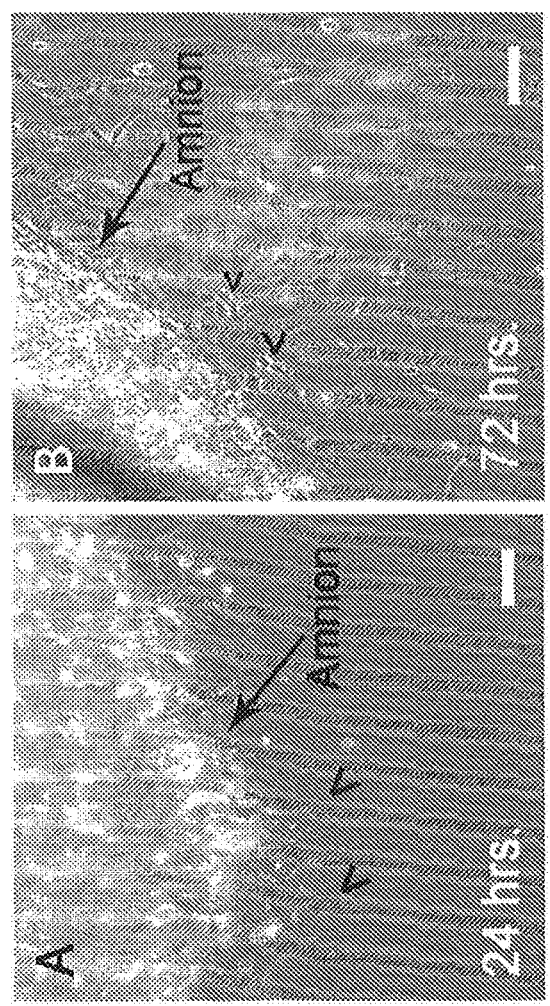
FIG. 1. Isolation and Propagation ADSCs: (A) Cells (>'s) migrate from amnion tissue explants (arrow) within 24 hours of plating. (B) By 72 hours numerous ameboid-shaped cells, can be observed migrating from the tissue explants. In addition, a number of doublets can be observed (>'s), indicative of cell proliferation. Explants are subsequently removed and the remaining small, ameboid shaped cells can be cultured indefinitely. Scale bars: A=50 µm; B=100 µm.

Amniotic membranes are isolated from embryonic day 18.5 (E18.5) rats. To avoid contamination with previously identified fetal stem cell populations residing in the rat placenta or umbilical cord, amnion tissue is isolated from the dorsal part of the amniotic sac. The amnion is mechanically peeled from the chorion and subsequently cut into small pieces and placed into tissue culture. Within 24 hours, cells begin to emerge from the tissue explants (FIG. 1A). By 72 hours numerous ameboid shaped cells migrate from the tissue pieces. Cell doublets are clearly visible, indicating cell proliferation (FIG. 1B). Immunocytochemical analysis of primary cultures reveal that by 24 hours fibronectin-positive (+) cells are visible at the edge of the tissue explants.

Figure 2:
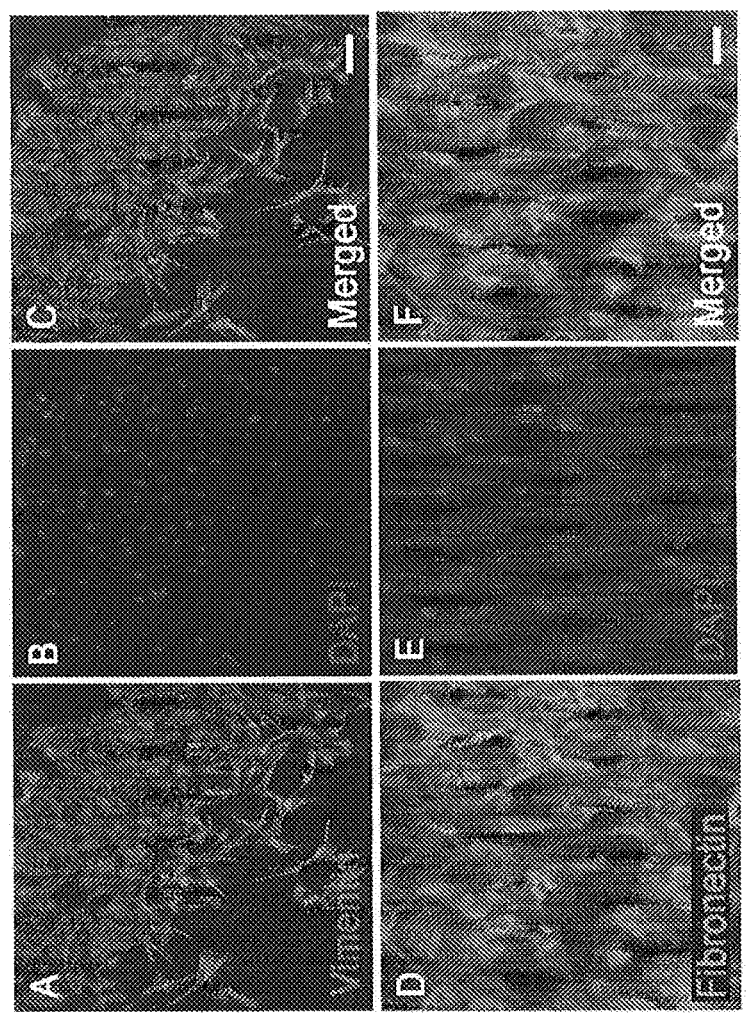
FIG. 2. Immunocytochemical Analysis of Primary ADSCs Cultures: (A-C) At 72 hours post-explanation close to 100% of the migrating cells migrating express the mesenchymal protein vimentin. (D-F) Further analysis reveals that these cells express fibronectin, consistent with a mesenchymal phenotype. Scale bars: A-C=100 µm; D-F=50 µm.

In contrast, cytokeratin-19 (CK-19)+ epithelial cell remain within the tissue pieces and do not migrate from the explants. At 72 hours close to 100% of the migrating cells are vimentin (FIG. 2, A-C) and fibronectin positive (FIG. 2, D-F).

Explants are removed after one week and the remaining cells are trypsinized and replated in 100 mm tissue culture dishes. By passage 5, the cell cultures predominately consist of rapidly dividing ameboid shaped cells, which are termed amnion-derived stem cells (ADSCs).

Initial characterization of the ADSCs is performed by flow cytometry. ADSCs express a number of mesenchymal cell surface markers, including CD29 and CD90, but are negative for the lymphohematopoietic markers CD45 and CD11b (FIG. 7).

Figure 3:
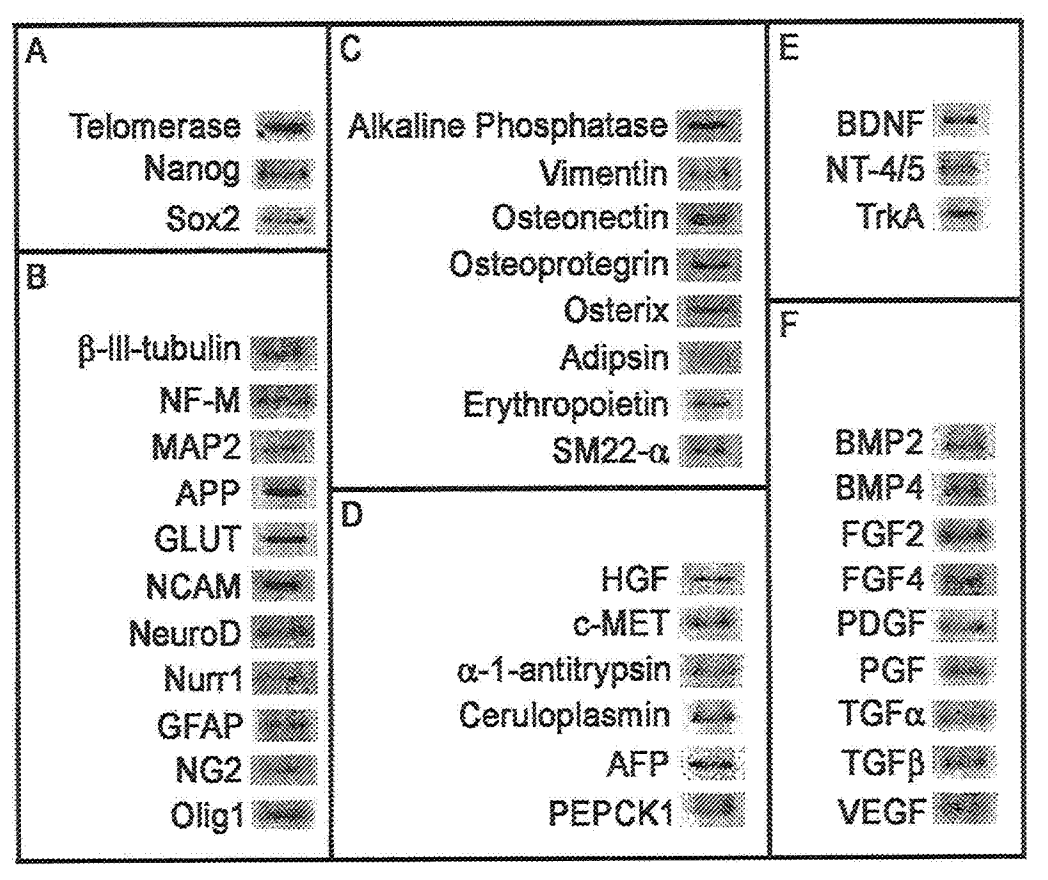

To further characterize ADSC gene expression, RNA is isolated from cultures at passage 3 and 12 and analyzed by RT-PCR. ADSCs express a number of transcription factors, including nanog and Sox2, involved in maintaining the pluripotency and self-renewal of ES cells (FIG. 3A). In addition, ADSCs express telomerase, a protein associated with the immortalization of ES cells (FIG. 3A). The expression of telomerase is consistent with the proliferative capacity of these cells; ADSCs are expanded greater than 50 passages in culture.

PCR analysis reveals that cultured ADSCs express genes of all three germinal layers. Specifically, ADSCs express a number of neuroectodermal genes of varying function (FIG. 3B).

Transcription factors involved in neural differentiation, such as NmT1 and NeuroD are express, and mRNA for the neuronal structural proteins MAP2 and NF-M are also detected. ADSCs also contain transcripts for GFAP and Olig 1, markers of astrocytes and oligodendrocytes, respectively. ADSCs do not express a number of other neural and ectodermal markers including, tyrosine hydroxylase, tau and pancytokeratin (data not shown).

Consistent with the flow cytometry data, ADSCs express a number of mesenchymal genes. For example, vimentin, an intermediate filament found in mesenchymal cells (FIG. 3C), as well as other genes normally express bone (osterix and alkaline phosphatase), fat (adipsin) and smooth muscle (SM22 □) are detected. The cells also contained mRNA for numerous endodermal genes (FIG. 3D) including, α-1-antitrypsin, an enzyme found in both the liver and lung. Furthermore, ADSCs express a number of neurotrophin genes (FIG. 3E), including brain-derived neurotrophic factor (BDNF), a molecule involved in neuron survival and synaptic plasticity, as well as a number of growth factors (FIG. 3F) that may play roles in embryonic development. Expression of osteopontin, TrkB, TrkC and GDNF in cultured ADSCs is not detected.

Figure 4:
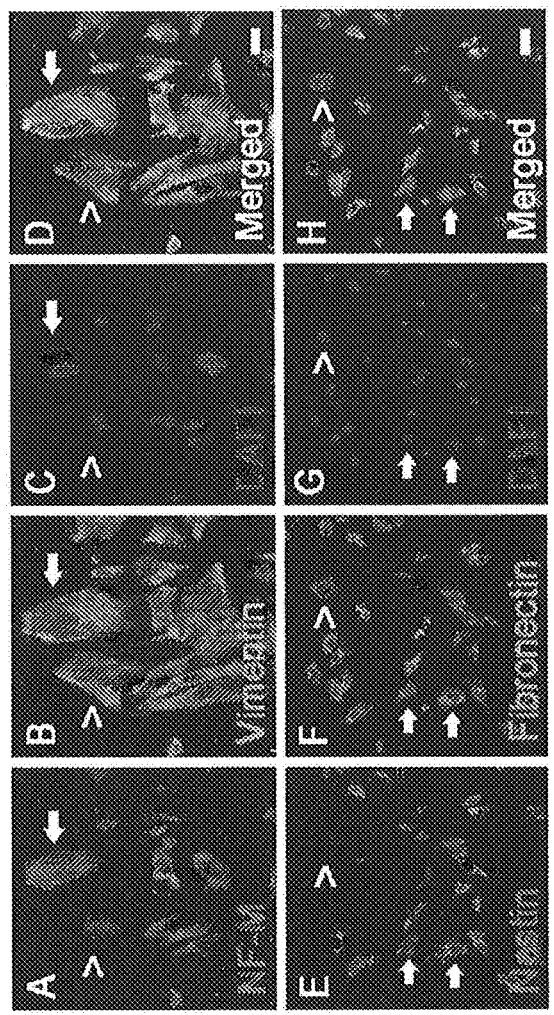
FIG. 4. ADSCs are Multidifferentiated: (A-D) A subpopulation of ADSCs co-express the mesenchymal protein vimentin and neuroectodermal neurofilament-M (NF-M) (arrow). Vimentin-positive (+)/NF-M-negative (−) cells are also evident (>). (E-H) A subset of ADSCs co-express the neural progenitor marker nestin and the mesenchymal protein fibronectin (arrows). Fibronectin+ cells that do not express nestin are also present (>). Scale bars: A-D=50 µm; E-H=100 µm.

To confirm PCR results and examine the co-expression of markers of different embryonic layers within single cells, immunocytochemistry is performed. Subpopulations of ADSCs are observed to be multidifferentiated, simultaneously expressing products of two distinct embryonic germ layers. For example, single ADSCs co-express the mesodermal protein, vimentin and the neuroectodermal protein, NF-M (FIG. 4, A-D). Other cells co-express the mesenchymal protein, fibronectin and the neural progenitor marker, nestin (FIG. 4, E-H). The multidifferentiated state of subpopulations of ADSCs raises the possibility that ADSCs are also multipotent, capable of differentiating to diverse cell types in vitro. To test this hypothesis, the ADSCs are subjected to a number of defined induction protocols designed to foster differentiation into distinct somatic cell types.

Example 3—Neural Differentiation of ADSCs

Figure 5:
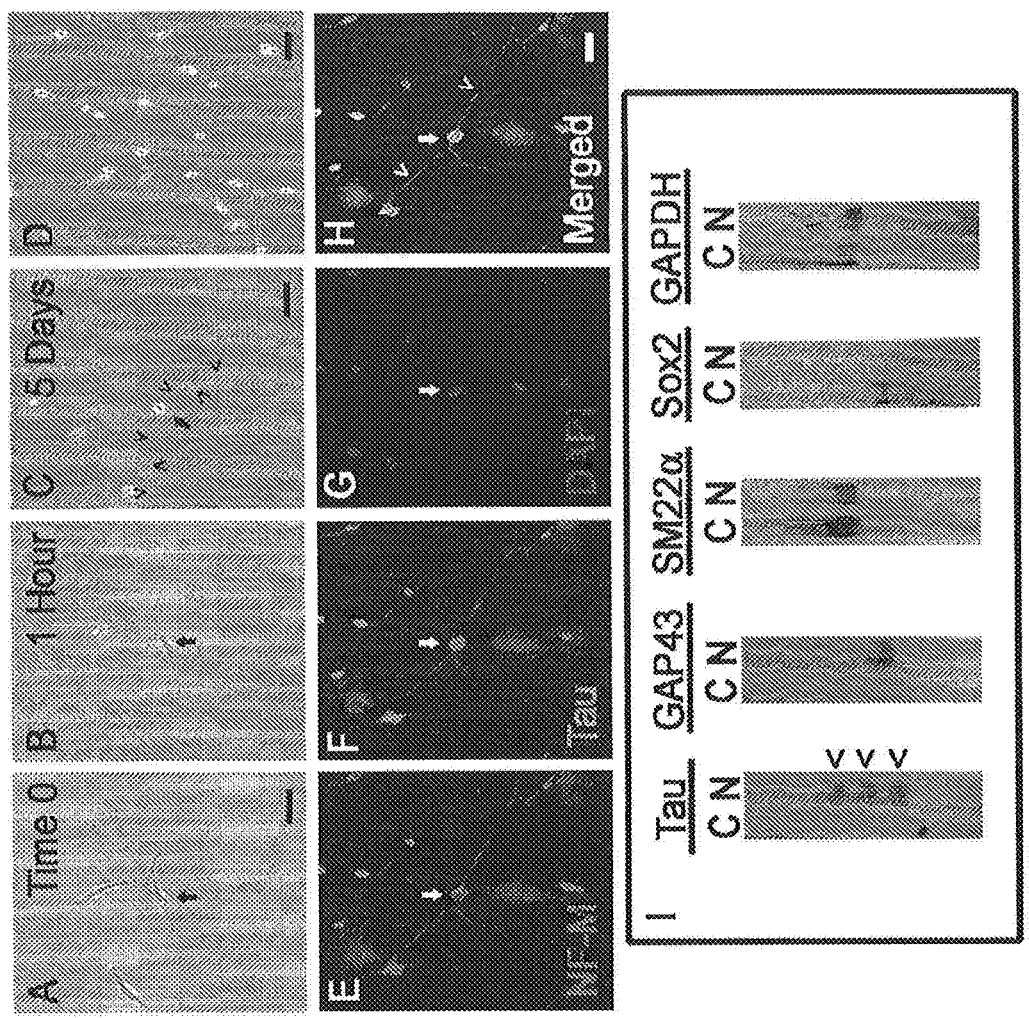
FIG. 5. Neuroectodermal differentiation of ADSCs: (A-C) Time-lapse images of a single ADSC (arrow) at 0, 1 hour and 5 days following exposure to NIM. ADSCs attain a neural morphology, exhibiting round, compact, refractile cell bodies (arrow), while elaborating processes (>'s) greater than 500 µm in length. (D) Cellular extensions of differentiated ADSCs make connections with neighboring cells and form complex neural networks similar to primary neural cultures. (E-H) Immunocytochemical analysis reveals the co-expression of tau and NFM throughout the cell body (arrow) and processes (>'s) of differentiated ADSCs. (I) PCR analysis of ADSCs exposed to NIM for one week up-regulate neural-specific genes, including GAP-43 and tau (three splice variants, >'s). Differentiated ADSCs down-regulate the neural stem cell marker Sox2, and the mesenchymal gene SM22α. GAPDH is utilized as a loading control. C=7 day serum-free control, N=7 day NIM treated ADSC cultures. Scale bars: A–H=100 µm.

To examine neuroectodermal potential, ADSCs are exposed to a defined neural induction medium (NIM). ADSCs responds slowly to the induction media assuming elongated fibroblastic morphologies within 24 hours (FIGS. 5, A and B). Over the next several days, greater than 7S % of the cells convert from flat, ameboid figures to cells displaying compact, light refractile cell bodies (FIG. 5C). ADSCs elaborate long processes (FIG. 5C) some extending more than 500 µm from the cell body. In many cases, the cellular processes form networks (FIG. 5D) with neighboring cells similar to those found in primary neural cultures.

Morphological changes of differentiated ADSCs are accompanied by consistent changes in gene expression. ADSCs maintain the expression of some neuronal genes such as NF-M, and up-regulate other neural genes (FIG. 5, E-H). For instance, tau, a microtubule associated protein found in mature neurons, is expressed only in NIM-treated cultures (FIG. 5, E-H). Differentiated ADSCs up-regulate additional neural specific genes including GAP43, while down-regulating mesenchymal genes such as SM22α (FIG. 5I). Moreover, Sox2 and NeuroD, two transcription factors found in undifferentiated neural stem cells, are appropriately down-regulated in differentiating ADSCs.

Example 4—Mesodermal Differentiation of ADSCs

Figure 6:
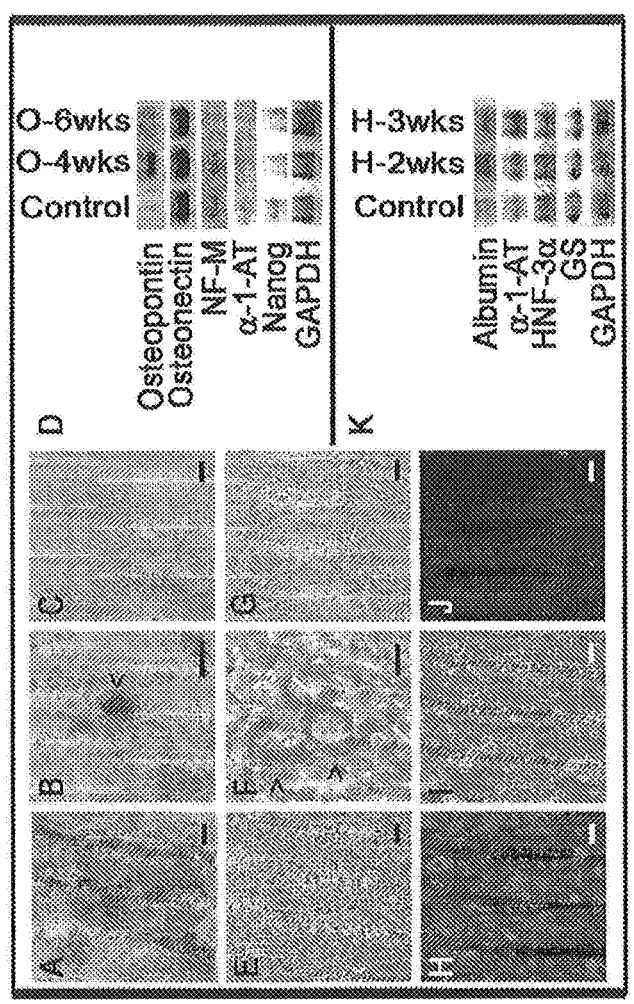
FIG. 6. Mesodermal Differentiation of ADSCs: Osteogenic Differentiation.

The potential of ADSC to differentiate into prototypical mesenchymal cell types: osteoblasts and adipocytes is also examined. ADSCs exposed to osteogenic induction media (OIM) for four weeks attain cuboidal morphologies and begin to form nodules, consistent with osteoblastic differentiation. At this time they are not depositing mineralized matrix. However, by six weeks treated cultures exhibit extensive mineralized matrix deposition, as denoted by alizarin red staining (FIGS. 6, A and B), consistent with a mature osteoblast phenotype. As expected, control cultures of ADSCs do not assume cuboidal morphologies or lay down mineralized matrix (FIG. 6C). PCR analysis reveals appropriate changes in gene expression with increased expression of osteopontin, and down-regulation of neural NF-M and endodermal α-1-antitrypsin (FIG. 6D). Consistent with differentiation, down-regulation of the pluripotency gene nanog is also observed.

ADSCs incubated in adipogenic induction media (AIM) acquired characteristics specific to mature adipocytes. After two weeks, cells begin to accumulate small cytoplasmic lipid droplets, as indicated by positive Oil Red O staining. With increasing time in culture, the lipid droplets coalesce, eventually filling most of the cytoplasm (FIGS. 6, E and F). In contrast, control cultures display no signs of lipid accumulation (FIG. 6G).

Example 5—Endodermal Differentiation of ADSCs

To further gauge plasticity, ADSC capacity for endodermal differentiation is examined. After exposure to hepatocyte induction media (HIM) ADSCs assume a cobblestone appearance (FIG. 6I), similar to mature hepatocytes. Differentiated cells demonstrate the ability to take up LDL from the media (FIGS. 6, H and I), an established hepatocyte trait. In contrast, control cells retain their ameboid morphology and do not take up LDL (FIG. 6J). In addition, PAS staining demonstrates that induced ADSC accumulate glycogen, another indication of hepatic differentiation. Moreover, liver-specific genes, including albumin and α-1-antitrypsin are up-regulated (FIG. 6K).

Example 6—Clonal Analysis of ADSCs

The observed plasticity of ADSCs may reflect the pluripotency of single cells or the presence of multiple progenitor cell types in the population. To distinguish between these possibilities, several clonal lines derived from single cells are established. Similar to parental populations of ADSCs, clonal lines consist of small ameboid shaped cells. Clonal lines are further analyzed by flow cytometry, RT-PCR and in vitro differentiation as described above.

Flow cytometry reveals that clonal populations (C1, C2) of ADSC have similar cell surface marker profiles when compare to parental ADSC populations (PS). All cultures are predominately positive for CD90 and CD29 (FIGS. 7, A and B). Some variability exists with regard to CD44 and CD31 (FIGS. 7, C and D), but all populations are uniformly negative for the lymphohematopoietic markers CD45 and CD 11b (FIGS. 7, E and F).

PCR analysis of clonal ADSCs recapitulates the expression profile found in the parental population (FIG. 8A). Clonal lines express genes representing all three germinal layers.

Immunocytochemical analysis reveals that close to 100% of the cells express the mesenchymal proteins vimentin and fibronectin. Moreover, consistent with the multidifferentiated state of the parental cultures, immunocytochemistry demonstrates that subpopulations of clonal ADSCs co-express mesenchymal and neuroectodermal proteins.

To assess plasticity, two clonal ADSC cell lines (C 1, C2) are exposed to defined induction protocols to determine their ability to multidifferentiate in vitro. In neural induction media clonal lines attain a neural phenotype. Morphology of NIM treated clonal ADSCs is similar to that obtained with parental population; treated cells display phase bright, refractile cell bodies (FIG. 8B) and long network forming processes. Similar to parental populations, upregulation of neural-specific genes is observed (see FIG. 5). Clonal lines exposed to adipogenic and osteogenic induction media accumulate fat droplets (FIG. 8B), and lay down mineralized matrix respectively (FIG. 8B). Moreover, under conditions conducive for hepatic differentiation, the clonal lines differentiate into presumptive hepatoctyes and exhibit LDL uptake (FIG. 8B). Collectively, this data suggests that parental ADSC cultures contain a population of the stem cells. Clonal lines derived from these cells possess the ability to undergo long-term self-renewal and multidifferentiation.

Example 7—In Vitro Characterization of ADSCs

To determine whether ADSCs assume neuronal functions in vivo and assess potential use for cellular therapy, donor cells are characterized after transplantation into the embryonic day 15.5 (E15.5) rat brain. For transplantation studies a clonal population of ADSCs which is utilized uniformly express GFP (FIG. 9AC). This clonal population demonstrates the stem cell characteristics of self-renewal and multi-potency. Close to 100% of the cells express vimentin (FIG. 9DG), while a subset express the neural progenitor marker nestin. (FIG. 9HK, arrowheads). Overexpression of the GFP gene does not affect the cells ability to respond morphologically to the in vitro neural induction protocol (FIG. 9L).

Example 8—Transplantation of GFP-Expressing ADSCs into the Embryonic Brain

One hundred to one hundred and fifty thousand donor GFP-expressing cells suspended in 2 to 3 μl of DMEM are injected into the telencephalic ventricles of each E15.5 recipient embryo. Invasion, migration, localization, phenotypic expression and long-term survival are assessed at various times post-transplantation.

Initially, short-term survival and engraftment 24 hours post-transplantation is characterized. At E16.5 donor cells are diffused throughout the ventricular system (FIG. 1QA). Some cells can also be identified within the parenchymal of the brain at this early time point (FIG. 10A, inset). By E17.5 discrete spherical clusters consisting of GFP+ cells are observed within the ventricles (FIG. 10B, arrow). A few clusters appear to have fused with the walls of the ventricles (FIG. 10C) and individual donor cells can be seen in the brain parenchyma (FIG. 10C, arrows). Widespread distribution of transplanted ADSCs is detected at later time points.

At E20.5 donor cells are consistently observed in multiple brain areas, including the cortex (FIG. 11AC, arrow) and midbrain (FIG. 11EG, arrow). Distribution of GFP+ cells at later postnatal time points seems to be random. In some animals, cells can be localized to the hippocampus and striatum while in others they are observed in the. Donor cells are often associated with blood vessels (FIG. 11D, arrow). These cells have crescent morphologies, similar to endothelial cells.

Example 9—Phenotypic Characterization of Transplanted ADSCs

The majority of donor cells that migrate into the parenchyma by P7, or 1 week postnatal, do not integrate within the normal cytoarchitecture of the brain. In most cases the ADSCs assume either elongated (FIG. 12A, arrows) or ameboid (FIG. 4E, arrows) morphologies. Mirr0l ing the expression pattern in culture, the majority of ADSC express vimentin (FIG. 12AD, arrows), while a subset also express Nestin (FIG. 12EH, arrows). Interestingly, a subpopulation of cells that migrates around blood vessels attained crescent morphologies and express vWF (FIG. 12IL, arrow), a blood glycoprotein involved in coagulation. These morphologic and phenotypic observations are consistent with an endothelial cell differentiation of donor ADSCs.

Some ADSCs that engraft in the brain attain neuronal morphologies: small cell body with long process extensions (fig SAC, arrow). Despite these morphological changes, no donor cells are found to upregulate any neural or glial markers, including β-III Tubulin (FIG. 13DG, arrows) and GFAP (FIG. 13HK, arrows). Transplanted ADSCs are also negative for the mature neural marker NeuN and the oligodendrocyte marker.

Example 10—Long-Term Survival of Donor Cells

Even in the absence of neuronal differentiation, donor ADSCs are able to survive in cortical (FIG. 14AC, arrows) and vascular regions (FIG. 14D, arrow) up to two and half months postnatal, the longest time examined. No evidence of a host inflammatory response or immunological rejection is observed, at early (P7) or later postnatal time points, as indicated by the absence of EDI+ reactive microglia cells (FIG. 14EH).

We claim:

1. A method for obtaining a pluripotent amnion-derived stem cell (ADSC) comprising:
   a. separating an amniotic membrane tissue sample from chorion of a mammalian embryo;
   b. culturing the amniotic membrane tissue sample in culture media without any enzymes or reagents to digest the amniotic membrane tissue sample;
   c. preparing a single-cell culture of adherent ADSCs isolated from the amniotic membrane tissue sample;
   d. culturing the ADSCs; and
   e. obtaining or isolating the ADSCs.

2. The method of claim 1, wherein the amniotic membrane tissue sample is washed and fragmented after step a. and before step b.

3. The method of claim 1, wherein the amniotic membrane tissue sample is cultured in Dulbecco's modified Eagle's medium (DMEM) supplemented with 20% fetal bovine serum (FBS).

* * * * *

SEQUENCE LISTING

<160> NUMBER OF SEQ ID NOS: 98

<210> SEQ ID NO 1
<211> LENGTH: 21
<212> TYPE: DNA
<213> ORGANISM: Unknown
<220> FEATURE:
<223> OTHER INFORMATION: primer sequence

<400> SEQUENCE: 1
ctgcgtgtgc gtgctctgga c        21

<210> SEQ ID NO 2
<211> LENGTH: 24
<212> TYPE: DNA
<213> ORGANISM: Unknown

-continued

```
<220> FEATURE:
<223> OTHER INFORMATION: primer sequence

<400> SEQUENCE: 2
cacctcagca aacagcttgt tctc                                           24

<210> SEQ ID NO 3
<211> LENGTH: 24
<212> TYPE: DNA
<213> ORGANISM: Unknown
<220> FEATURE:
<223> OTHER INFORMATION: primer sequence

<400> SEQUENCE: 3
tgctctgcac agagactggt aagg                                           24

<210> SEQ ID NO 4
<211> LENGTH: 24
<212> TYPE: DNA
<213> ORGANISM: Unknown
<220> FEATURE:
<223> OTHER INFORMATION: primer sequence

<400> SEQUENCE: 4
tctggttgct ccaggttggg ttgg                                           24

<210> SEQ ID NO 5
<211> LENGTH: 24
<212> TYPE: DNA
<213> ORGANISM: Unknown
<220> FEATURE:
<223> OTHER INFORMATION: primer sequence

<400> SEQUENCE: 5
acatgatgga gacggagctg aagc                                           24

<210> SEQ ID NO 6
<211> LENGTH: 24
<212> TYPE: DNA
<213> ORGANISM: Unknown
<220> FEATURE:
<223> OTHER INFORMATION: primer sequence

<400> SEQUENCE: 6
gctgctcctg catcatgctg tagc                                           24

<210> SEQ ID NO 7
<211> LENGTH: 23
<212> TYPE: DNA
<213> ORGANISM: Unknown
<220> FEATURE:
<223> OTHER INFORMATION: primer sequence

<400> SEQUENCE: 7
tgaccaaatc atacagcgag agc                                            23

<210> SEQ ID NO 8
<211> LENGTH: 24
<212> TYPE: DNA
<213> ORGANISM: Unknown
<220> FEATURE:
<223> OTHER INFORMATION: primer sequence

<400> SEQUENCE: 8
agaagttgcc attgatgctg agcg                                           24
```

```
<210> SEQ ID NO 9
<211> LENGTH: 24
<212> TYPE: DNA
<213> ORGANISM: Unknown
<220> FEATURE:
<223> OTHER INFORMATION: primer sequence

<400> SEQUENCE: 9
ctcccggagg aactgcactt cggc                                              24

<210> SEQ ID NO 10
<211> LENGTH: 24
<212> TYPE: DNA
<213> ORGANISM: Unknown
<220> FEATURE:
<223> OTHER INFORMATION: primer sequence

<400> SEQUENCE: 10
gtgtcttcct ctgctcgatc atat                                              24

<210> SEQ ID NO 11
<211> LENGTH: 24
<212> TYPE: DNA
<213> ORGANISM: Unknown
<220> FEATURE:
<223> OTHER INFORMATION: primer sequence

<400> SEQUENCE: 11
tgctcaagtc cctagactgg aacg                                              24

<210> SEQ ID NO 12
<211> LENGTH: 26
<212> TYPE: DNA
<213> ORGANISM: Unknown
<220> FEATURE:
<223> OTHER INFORMATION: primer sequence

<400> SEQUENCE: 12
cttctcgggc tctgtcagtg gtgtgg                                            26

<210> SEQ ID NO 13
<211> LENGTH: 24
<212> TYPE: DNA
<213> ORGANISM: Unknown
<220> FEATURE:
<223> OTHER INFORMATION: primer sequence

<400> SEQUENCE: 13
agtttcttgg tctctgggga cagc                                              24

<210> SEQ ID NO 14
<211> LENGTH: 24
<212> TYPE: DNA
<213> ORGANISM: Unknown
<220> FEATURE:
<223> OTHER INFORMATION: primer sequence

<400> SEQUENCE: 14
aactgatggt caggatcgac aggg                                              24

<210> SEQ ID NO 15
<211> LENGTH: 24
<212> TYPE: DNA
<213> ORGANISM: Unknown
<220> FEATURE:
<223> OTHER INFORMATION: primer sequence
```

<400> SEQUENCE: 15
tgctcatcag caaagtgcgt gagg                                              24

<210> SEQ ID NO 16
<211> LENGTH: 24
<212> TYPE: DNA
<213> ORGANISM: Unknown
<220> FEATURE:
<223> OTHER INFORMATION: primer sequence

<400> SEQUENCE: 16
atggccagca tctgctcatc cacc                                              24

<210> SEQ ID NO 17
<211> LENGTH: 24
<212> TYPE: DNA
<213> ORGANISM: Unknown
<220> FEATURE:
<223> OTHER INFORMATION: primer sequence

<400> SEQUENCE: 17
ctcgacttca gccagtcctc ttcg                                              24

<210> SEQ ID NO 18
<211> LENGTH: 24
<212> TYPE: DNA
<213> ORGANISM: Unknown
<220> FEATURE:
<223> OTHER INFORMATION: primer sequence

<400> SEQUENCE: 18
tctttgcgct ctacggtgat gtgc                                              24

<210> SEQ ID NO 19
<211> LENGTH: 24
<212> TYPE: DNA
<213> ORGANISM: Unknown
<220> FEATURE:
<223> OTHER INFORMATION: primer sequence

<400> SEQUENCE: 19
taaccaacac tagcggaacg atgg                                              24

<210> SEQ ID NO 20
<211> LENGTH: 24
<212> TYPE: DNA
<213> ORGANISM: Unknown
<220> FEATURE:
<223> OTHER INFORMATION: primer sequence

<400> SEQUENCE: 20
tacctctggc actgaactga gacc                                              24

<210> SEQ ID NO 21
<211> LENGTH: 24
<212> TYPE: DNA
<213> ORGANISM: Unknown
<220> FEATURE:
<223> OTHER INFORMATION: primer sequence

<400> SEQUENCE: 21
ggctttgaag cagcatggct gaac                                              24

<210> SEQ ID NO 22

<211> LENGTH: 24
<212> TYPE: DNA
<213> ORGANISM: Unknown
<220> FEATURE:
<223> OTHER INFORMATION: primer sequence

<400> SEQUENCE: 22
ggcctgatca caaaccctgc ttgg                                           24

<210> SEQ ID NO 23
<211> LENGTH: 24
<212> TYPE: DNA
<213> ORGANISM: Unknown
<220> FEATURE:
<223> OTHER INFORMATION: primer sequence

<400> SEQUENCE: 23
atgctgtgct gtatgagaag aacc                                           24

<210> SEQ ID NO 24
<211> LENGTH: 24
<212> TYPE: DNA
<213> ORGANISM: Unknown
<220> FEATURE:
<223> OTHER INFORMATION: primer sequence

<400> SEQUENCE: 24
tcaggcatgt tcttggtcag cctc                                           24

<210> SEQ ID NO 25
<211> LENGTH: 24
<212> TYPE: DNA
<213> ORGANISM: Unknown
<220> FEATURE:
<223> OTHER INFORMATION: primer sequence

<400> SEQUENCE: 25
agtttcttgg tctctgggga cagc                                           24

<210> SEQ ID NO 26
<211> LENGTH: 24
<212> TYPE: DNA
<213> ORGANISM: Unknown
<220> FEATURE:
<223> OTHER INFORMATION: primer sequence

<400> SEQUENCE: 26
aactgatggt caggatcgac aggg                                           24

<210> SEQ ID NO 27
<211> LENGTH: 24
<212> TYPE: DNA
<213> ORGANISM: Unknown
<220> FEATURE:
<223> OTHER INFORMATION: primer sequence

<400> SEQUENCE: 27
agctgaacca gcttcgagcc aagg                                           24

<210> SEQ ID NO 28
<211> LENGTH: 24
<212> TYPE: DNA
<213> ORGANISM: Unknown
<220> FEATURE:
<223> OTHER INFORMATION: primer sequence

<400> SEQUENCE: 28

```
ggaagcaacg tctgtgaggt ctgc                                              24

<210> SEQ ID NO 29
<211> LENGTH: 24
<212> TYPE: DNA
<213> ORGANISM: Unknown
<220> FEATURE:
<223> OTHER INFORMATION: primer sequence

<400> SEQUENCE: 29
tggtagccca gaagcaggta ctcc                                              24

<210> SEQ ID NO 30
<211> LENGTH: 24
<212> TYPE: DNA
<213> ORGANISM: Unknown
<220> FEATURE:
<223> OTHER INFORMATION: primer sequence

<400> SEQUENCE: 30
tgtcctgcag tcagctcaga ttgc                                              24

<210> SEQ ID NO 31
<211> LENGTH: 24
<212> TYPE: DNA
<213> ORGANISM: Unknown
<220> FEATURE:
<223> OTHER INFORMATION: primer sequence

<400> SEQUENCE: 31
gacggcgaca gagtctcatc gagg                                              24

<210> SEQ ID NO 32
<211> LENGTH: 24
<212> TYPE: DNA
<213> ORGANISM: Unknown
<220> FEATURE:
<223> OTHER INFORMATION: primer sequence

<400> SEQUENCE: 32
cagcagtccg gctcaggtga atgc                                              24

<210> SEQ ID NO 33
<211> LENGTH: 24
<212> TYPE: DNA
<213> ORGANISM: Unknown
<220> FEATURE:
<223> OTHER INFORMATION: primer sequence

<400> SEQUENCE: 33
aagaccccag ttactggcga cagc                                              24

<210> SEQ ID NO 34
<211> LENGTH: 24
<212> TYPE: DNA
<213> ORGANISM: Unknown
<220> FEATURE:
<223> OTHER INFORMATION: primer sequence

<400> SEQUENCE: 34
cctttccgat ggcctcatcc atct                                              24

<210> SEQ ID NO 35
<211> LENGTH: 24
<212> TYPE: DNA
```

```
<213> ORGANISM: Unknown
<220> FEATURE:
<223> OTHER INFORMATION: primer sequence

<400> SEQUENCE: 35
cacctcagca aacagcttgt tctc                                              24

<210> SEQ ID NO 36
<211> LENGTH: 24
<212> TYPE: DNA
<213> ORGANISM: Unknown
<220> FEATURE:
<223> OTHER INFORMATION: primer sequence

<400> SEQUENCE: 36
cagagtgacg gtgagcgagt tggc                                              24

<210> SEQ ID NO 37
<211> LENGTH: 24
<212> TYPE: DNA
<213> ORGANISM: Unknown
<220> FEATURE:
<223> OTHER INFORMATION: primer sequence

<400> SEQUENCE: 37
ggaatggacc tgcaagccaa tagc                                              24

<210> SEQ ID NO 38
<211> LENGTH: 24
<212> TYPE: DNA
<213> ORGANISM: Unknown
<220> FEATURE:
<223> OTHER INFORMATION: primer sequence

<400> SEQUENCE: 38
gaattcccac ctcgagtctg aacc                                              24

<210> SEQ ID NO 39
<211> LENGTH: 24
<212> TYPE: DNA
<213> ORGANISM: Unknown
<220> FEATURE:
<223> OTHER INFORMATION: primer sequence

<400> SEQUENCE: 39
ccaacgagaa ggtggaattg cagg                                              24

<210> SEQ ID NO 40
<211> LENGTH: 24
<212> TYPE: DNA
<213> ORGANISM: Unknown
<220> FEATURE:
<223> OTHER INFORMATION: primer sequence

<400> SEQUENCE: 40
gccatcttta cattgagcag gtcc                                              24

<210> SEQ ID NO 41
<211> LENGTH: 24
<212> TYPE: DNA
<213> ORGANISM: Unknown
<220> FEATURE:
<223> OTHER INFORMATION: primer sequence

<400> SEQUENCE: 41
cggaagctgc agaagagatg gtgg                                              24
```

-continued

<210> SEQ ID NO 42
<211> LENGTH: 24
<212> TYPE: DNA
<213> ORGANISM: Unknown
<220> FEATURE:
<223> OTHER INFORMATION: primer sequence

<400> SEQUENCE: 42
tgtcctgctc cttgatgcca aagc                                          24

<210> SEQ ID NO 43
<211> LENGTH: 24
<212> TYPE: DNA
<213> ORGANISM: Unknown
<220> FEATURE:
<223> OTHER INFORMATION: primer sequence

<400> SEQUENCE: 43
tcggaggaga aggcgcatta cagc                                          24

<210> SEQ ID NO 44
<211> LENGTH: 24
<212> TYPE: DNA
<213> ORGANISM: Unknown
<220> FEATURE:
<223> OTHER INFORMATION: primer sequence

<400> SEQUENCE: 44
tcctcatggc tgtgaaactc gtgg                                          24

<210> SEQ ID NO 45
<211> LENGTH: 24
<212> TYPE: DNA
<213> ORGANISM: Unknown
<220> FEATURE:
<223> OTHER INFORMATION: primer sequence

<400> SEQUENCE: 45
acgagtgatg aatgcgtgta ctgc                                          24

<210> SEQ ID NO 46
<211> LENGTH: 24
<212> TYPE: DNA
<213> ORGANISM: Unknown
<220> FEATURE:
<223> OTHER INFORMATION: primer sequence

<400> SEQUENCE: 46
tctcgttctc tcaatctcgt ctgg                                          24

<210> SEQ ID NO 47
<211> LENGTH: 24
<212> TYPE: DNA
<213> ORGANISM: Unknown
<220> FEATURE:
<223> OTHER INFORMATION: primer sequence

<400> SEQUENCE: 47
ccttctcaag caccaatggt ctcc                                          24

<210> SEQ ID NO 48
<211> LENGTH: 24
<212> TYPE: DNA
<213> ORGANISM: Unknown
<220> FEATURE:

<223> OTHER INFORMATION: primer sequence

<400> SEQUENCE: 48
actgcctgca tatccaccac tgcc                                        24

<210> SEQ ID NO 49
<211> LENGTH: 24
<212> TYPE: DNA
<213> ORGANISM: Unknown
<220> FEATURE:
<223> OTHER INFORMATION: primer sequence

<400> SEQUENCE: 49
cagtgcaagt gaatggcacg cacg                                        24

<210> SEQ ID NO 50
<211> LENGTH: 24
<212> TYPE: DNA
<213> ORGANISM: Unknown
<220> FEATURE:
<223> OTHER INFORMATION: primer sequence

<400> SEQUENCE: 50
tcaatccacg gcacgtaggt tgcc                                        24

<210> SEQ ID NO 51
<211> LENGTH: 24
<212> TYPE: DNA
<213> ORGANISM: Unknown
<220> FEATURE:
<223> OTHER INFORMATION: primer sequence

<400> SEQUENCE: 51
tctccttcca gtccacaaac gacc                                        24

<210> SEQ ID NO 52
<211> LENGTH: 24
<212> TYPE: DNA
<213> ORGANISM: Unknown
<220> FEATURE:
<223> OTHER INFORMATION: primer sequence

<400> SEQUENCE: 52
cttccctttc taactgatga tctg                                        24

<210> SEQ ID NO 53
<211> LENGTH: 24
<212> TYPE: DNA
<213> ORGANISM: Unknown
<220> FEATURE:
<223> OTHER INFORMATION: primer sequence

<400> SEQUENCE: 53
tcgtgacaac tacggtgaac tggc                                        24

<210> SEQ ID NO 54
<211> LENGTH: 24
<212> TYPE: DNA
<213> ORGANISM: Unknown
<220> FEATURE:
<223> OTHER INFORMATION: primer sequence

<400> SEQUENCE: 54
tgttctgtct cagcgagaca ctgg                                        24

-continued

```
<210> SEQ ID NO 55
<211> LENGTH: 24
<212> TYPE: DNA
<213> ORGANISM: Unknown
<220> FEATURE:
<223> OTHER INFORMATION: primer sequence

<400> SEQUENCE: 55
cccacttgaa caaaggcatc aagc                                              24

<210> SEQ ID NO 56
<211> LENGTH: 24
<212> TYPE: DNA
<213> ORGANISM: Unknown
<220> FEATURE:
<223> OTHER INFORMATION: primer sequence

<400> SEQUENCE: 56
ggtcctatct ggaattccca ctgg                                              24

<210> SEQ ID NO 57
<211> LENGTH: 24
<212> TYPE: DNA
<213> ORGANISM: Unknown
<220> FEATURE:
<223> OTHER INFORMATION: primer sequence

<400> SEQUENCE: 57
gcaggctcca tgaacatgtc atcc                                              24

<210> SEQ ID NO 58
<211> LENGTH: 24
<212> TYPE: DNA
<213> ORGANISM: Unknown
<220> FEATURE:
<223> OTHER INFORMATION: primer sequence

<400> SEQUENCE: 58
gctgaacctg agaagcctgt gtcc                                              24

<210> SEQ ID NO 59
<211> LENGTH: 24
<212> TYPE: DNA
<213> ORGANISM: Unknown
<220> FEATURE:
<223> OTHER INFORMATION: primer sequence

<400> SEQUENCE: 59
caagcaatcc agaggtacgc tacg                                              24

<210> SEQ ID NO 60
<211> LENGTH: 24
<212> TYPE: DNA
<213> ORGANISM: Unknown
<220> FEATURE:
<223> OTHER INFORMATION: primer sequence

<400> SEQUENCE: 60
gcacaggata ttacaggatg gtcc                                              24

<210> SEQ ID NO 61
<211> LENGTH: 24
<212> TYPE: DNA
<213> ORGANISM: Unknown
<220> FEATURE:
<223> OTHER INFORMATION: primer sequence
```

```
<400> SEQUENCE: 61
ccctagtgaa gtctgagatg aacg                                              24

<210> SEQ ID NO 62
<211> LENGTH: 24
<212> TYPE: DNA
<213> ORGANISM: Unknown
<220> FEATURE:
<223> OTHER INFORMATION: primer sequence

<400> SEQUENCE: 62
ggaatctcgg aattctggca ggac                                              24

<210> SEQ ID NO 63
<211> LENGTH: 24
<212> TYPE: DNA
<213> ORGANISM: Unknown
<220> FEATURE:
<223> OTHER INFORMATION: primer sequence

<400> SEQUENCE: 63
gacaaggcag ttccagcatg ctgc                                              24

<210> SEQ ID NO 64
<211> LENGTH: 24
<212> TYPE: DNA
<213> ORGANISM: Unknown
<220> FEATURE:
<223> OTHER INFORMATION: primer sequence

<400> SEQUENCE: 64
gctggcagca cgttgaggca atgc                                              24

<210> SEQ ID NO 65
<211> LENGTH: 25
<212> TYPE: DNA
<213> ORGANISM: Unknown
<220> FEATURE:
<223> OTHER INFORMATION: primer sequence

<400> SEQUENCE: 65
ctacagttgc tccaacgttg ccagg                                             25

<210> SEQ ID NO 66
<211> LENGTH: 24
<212> TYPE: DNA
<213> ORGANISM: Unknown
<220> FEATURE:
<223> OTHER INFORMATION: primer sequence

<400> SEQUENCE: 66
agtaaccagc ttccaggcgt ttgg                                              24

<210> SEQ ID NO 67
<211> LENGTH: 24
<212> TYPE: DNA
<213> ORGANISM: Unknown
<220> FEATURE:
<223> OTHER INFORMATION: primer sequence

<400> SEQUENCE: 67
gacaaggcag ttccagcatg ctgc                                              24

<210> SEQ ID NO 68
<211> LENGTH: 24
```

<212> TYPE: DNA
<213> ORGANISM: Unknown
<220> FEATURE:
<223> OTHER INFORMATION: primer sequence

<400> SEQUENCE: 68
gctggcagca cgttgaggca atgc                                          24

<210> SEQ ID NO 69
<211> LENGTH: 24
<212> TYPE: DNA
<213> ORGANISM: Unknown
<220> FEATURE:
<223> OTHER INFORMATION: primer sequence

<400> SEQUENCE: 69
ctcctcagct gcataatggt ctgg                                          24

<210> SEQ ID NO 70
<211> LENGTH: 24
<212> TYPE: DNA
<213> ORGANISM: Unknown
<220> FEATURE:
<223> OTHER INFORMATION: primer sequence

<400> SEQUENCE: 70
tggggttcat catggccagg ttgg                                          24

<210> SEQ ID NO 71
<211> LENGTH: 24
<212> TYPE: DNA
<213> ORGANISM: Unknown
<220> FEATURE:
<223> OTHER INFORMATION: primer sequence

<400> SEQUENCE: 71
ccaaactgga ggagatgatg ctgc                                          24

<210> SEQ ID NO 72
<211> LENGTH: 24
<212> TYPE: DNA
<213> ORGANISM: Unknown
<220> FEATURE:
<223> OTHER INFORMATION: primer sequence

<400> SEQUENCE: 72
caaagtgttg ccactgttgg gtgc                                          24

<210> SEQ ID NO 73
<211> LENGTH: 24
<212> TYPE: DNA
<213> ORGANISM: Unknown
<220> FEATURE:
<223> OTHER INFORMATION: primer sequence

<400> SEQUENCE: 73
tcctcctttt ccttctcctc ctcc                                          24

<210> SEQ ID NO 74
<211> LENGTH: 24
<212> TYPE: DNA
<213> ORGANISM: Unknown
<220> FEATURE:
<223> OTHER INFORMATION: primer sequence

<400> SEQUENCE: 74

-continued gcacatagga ctgtttagcc ttgc                                          24

<210> SEQ ID NO 75
<211> LENGTH: 22
<212> TYPE: DNA
<213> ORGANISM: Unknown
<220> FEATURE:
<223> OTHER INFORMATION: primer sequence

<400> SEQUENCE: 75
gtggctgtca aggcactgaa gg                                            22

<210> SEQ ID NO 76
<211> LENGTH: 21
<212> TYPE: DNA
<213> ORGANISM: Unknown
<220> FEATURE:
<223> OTHER INFORMATION: primer sequence

<400> SEQUENCE: 76
tgttggagag ctggtaccag g                                             21

<210> SEQ ID NO 77
<211> LENGTH: 24
<212> TYPE: DNA
<213> ORGANISM: Unknown
<220> FEATURE:
<223> OTHER INFORMATION: primer sequence

<400> SEQUENCE: 77
ctgtcttcta gtgttgctgc ttcc                                          24

<210> SEQ ID NO 78
<211> LENGTH: 24
<212> TYPE: DNA
<213> ORGANISM: Unknown
<220> FEATURE:
<223> OTHER INFORMATION: primer sequence

<400> SEQUENCE: 78
ttctgagtca ctaacctggt gtcc                                          24

<210> SEQ ID NO 79
<211> LENGTH: 24
<212> TYPE: DNA
<213> ORGANISM: Unknown
<220> FEATURE:
<223> OTHER INFORMATION: primer sequence

<400> SEQUENCE: 79
acactgtgag gagtttccat cacg                                          24

<210> SEQ ID NO 80
<211> LENGTH: 24
<212> TYPE: DNA
<213> ORGANISM: Unknown
<220> FEATURE:
<223> OTHER INFORMATION: primer sequence

<400> SEQUENCE: 80
ttccagccca cgtcactgaa gtcc                                          24

<210> SEQ ID NO 81
<211> LENGTH: 24
<212> TYPE: DNA
<213> ORGANISM: Unknown

<220> FEATURE:
<223> OTHER INFORMATION: primer sequence

<400> SEQUENCE: 81
gtatcctggt agctgtgtgt cagg                                            24

<210> SEQ ID NO 82
<211> LENGTH: 24
<212> TYPE: DNA
<213> ORGANISM: Unknown
<220> FEATURE:
<223> OTHER INFORMATION: primer sequence

<400> SEQUENCE: 82
agaccactgt ctcagagtgg cagc                                            24

<210> SEQ ID NO 83
<211> LENGTH: 24
<212> TYPE: DNA
<213> ORGANISM: Unknown
<220> FEATURE:
<223> OTHER INFORMATION: primer sequence

<400> SEQUENCE: 83
ccacctgcaa gaccatcgac atgg                                            24

<210> SEQ ID NO 84
<211> LENGTH: 24
<212> TYPE: DNA
<213> ORGANISM: Unknown
<220> FEATURE:
<223> OTHER INFORMATION: primer sequence

<400> SEQUENCE: 84
ggactgatcc cattgatttc cacg                                            24

<210> SEQ ID NO 85
<211> LENGTH: 24
<212> TYPE: DNA
<213> ORGANISM: Unknown
<220> FEATURE:
<223> OTHER INFORMATION: primer sequence

<400> SEQUENCE: 85
tttctgctct cttgggtgca ctgg                                            24

<210> SEQ ID NO 86
<211> LENGTH: 24
<212> TYPE: DNA
<213> ORGANISM: Unknown
<220> FEATURE:
<223> OTHER INFORMATION: primer sequence

<400> SEQUENCE: 86
tggcttgtca catctgcaag tacg                                            24

<210> SEQ ID NO 87
<211> LENGTH: 24
<212> TYPE: DNA
<213> ORGANISM: Unknown
<220> FEATURE:
<223> OTHER INFORMATION: primer sequence

<400> SEQUENCE: 87
cacttgcttc ttgcaggtcc tagc                                            24

<210> SEQ ID NO 88
<211> LENGTH: 24
<212> TYPE: DNA
<213> ORGANISM: Unknown
<220> FEATURE:
<223> OTHER INFORMATION: primer sequence

<400> SEQUENCE: 88
tgcctttgtc gtctccagaa tagg                                              24

<210> SEQ ID NO 89
<211> LENGTH: 24
<212> TYPE: DNA
<213> ORGANISM: Unknown
<220> FEATURE:
<223> OTHER INFORMATION: primer sequence

<400> SEQUENCE: 89
aagcggctct actgcaagaa cggc                                              24

<210> SEQ ID NO 90
<211> LENGTH: 24
<212> TYPE: DNA
<213> ORGANISM: Unknown
<220> FEATURE:
<223> OTHER INFORMATION: primer sequence

<400> SEQUENCE: 90
tccgagttta tactgcccag ttcg                                              24

<210> SEQ ID NO 91
<211> LENGTH: 24
<212> TYPE: DNA
<213> ORGANISM: Unknown
<220> FEATURE:
<223> OTHER INFORMATION: primer sequence

<400> SEQUENCE: 91
gactacctgc tgggcctcaa aagg                                              24

<210> SEQ ID NO 92
<211> LENGTH: 24
<212> TYPE: DNA
<213> ORGANISM: Unknown
<220> FEATURE:
<223> OTHER INFORMATION: primer sequence

<400> SEQUENCE: 92
ggaagtgggt taccttcatg gtcg                                              24

<210> SEQ ID NO 93
<211> LENGTH: 24
<212> TYPE: DNA
<213> ORGANISM: Unknown
<220> FEATURE:
<223> OTHER INFORMATION: primer sequence

<400> SEQUENCE: 93
agcgactggc tcgaagtcag atcc                                              24

<210> SEQ ID NO 94
<211> LENGTH: 24
<212> TYPE: DNA
<213> ORGANISM: Unknown
<220> FEATURE:
<223> OTHER INFORMATION: primer sequence

```
<400> SEQUENCE: 94
tccaggtgct cctctaacct cacc                                              24

<210> SEQ ID NO 95
<211> LENGTH: 24
<212> TYPE: DNA
<213> ORGANISM: Unknown
<220> FEATURE:
<223> OTHER INFORMATION: primer sequence

<400> SEQUENCE: 95
ctgtactcag tgtcacagca cagc                                              24

<210> SEQ ID NO 96
<211> LENGTH: 24
<212> TYPE: DNA
<213> ORGANISM: Unknown
<220> FEATURE:
<223> OTHER INFORMATION: primer sequence

<400> SEQUENCE: 96
catagtaagc aaatcgtgcc gtgc                                              24

<210> SEQ ID NO 97
<211> LENGTH: 24
<212> TYPE: DNA
<213> ORGANISM: Unknown
<220> FEATURE:
<223> OTHER INFORMATION: primer sequence

<400> SEQUENCE: 97
tgtgaacgga tttggccgta tcgg                                              24

<210> SEQ ID NO 98
<211> LENGTH: 24
<212> TYPE: DNA
<213> ORGANISM: Unknown
<220> FEATURE:
<223> OTHER INFORMATION: primer sequence

<400> SEQUENCE: 98
atgccagtga gcttcccgtt cagc                                              24
```